US007305985B2

(12) United States Patent
    Brain

(10) Patent No.: US 7,305,985 B2
(45) Date of Patent: *Dec. 11, 2007

(54) LARYNGEAL MASK AIRWAY DEVICE

(75) Inventor: Archibald Ian Jeremy Brain, Surrey (GB)

(73) Assignee: The Laryngeal Mask Company Limited, The Seychelles (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/350,470

(22) Filed: Feb. 10, 2006

(65) Prior Publication Data

US 2006/0124132 A1    Jun. 15, 2006

Related U.S. Application Data

(63) Continuation of application No. 10/225,678, filed on Aug. 22, 2002, now abandoned, which is a continuation of application No. 09/289,319, filed on Apr. 9, 1999, now Pat. No. 6,439,232.

(30) Foreign Application Priority Data

Aug. 13, 1998  (GB) .................................. 9817537.5

(51) Int. Cl.
    *A61M 16/00*    (2006.01)
(52) U.S. Cl. .............................. 128/200.26; 128/207.14
(58) Field of Classification Search ........... 128/200.26, 128/207.14, 207.15, 207.16
    See application file for complete search history.

(56) References Cited

U.S. PATENT DOCUMENTS 2,862,498 A    12/1958  Weekes (Continued)

FOREIGN PATENT DOCUMENTS

CA    2067782    6/1999

(Continued)

OTHER PUBLICATIONS

Abdelatti, "A Cuff Pressure Controller for Tracheal Tubes and Laryngeal Mask Airway," Anaesthesia, 1999, vol. 54, pp. 981-986.

(Continued)

*Primary Examiner*—Teena Mitchell
(74) *Attorney, Agent, or Firm*—Wilmer, Cutler, Pickering, Hale and Dorr LLP

(57) ABSTRACT

A laryngeal-mask airway device including provision for drainage of the oesophagus comprises an inflatable main-cuff and a backplate having a laryngeal-side and a pharyngeal-side. The backplate also has an external tube-joint adjacent to the proximal region of the main-cuff. The backplate is hermetically bonded to the periphery of the main-cuff establishing separation between a laryngeal-chamber region and a pharyngeal region. An distally open evacuation tube includes a distal portion which longitudinally traverses the interior of the distal region of the main-cuff in sealed relation therewith for operative engagement and communication with the inlet of the oesophagus. The evacuation tube traverses the laryngeal-chamber region generally adjacent to the laryngeal-side of the backplate and passages through a proximally located tube-joint to the pharyngeal region. An airway tube also extends into the tube-joint for communication with an airway port to provide a flowpath between the airway tube and laryngeal-chamber region.

33 Claims, 10 Drawing Sheets

U.S. PATENT DOCUMENTS

| | | | |
|---|---|---|---|
| 3,554,673 A | 1/1971 | Schwartz et al. | |
| 3,683,908 A | 8/1972 | Michael et al. | |
| 3,931,822 A | 1/1976 | Marici | |
| 4,104,357 A | 8/1978 | Blair | |
| 4,231,365 A | 11/1980 | Scarberry | |
| 4,256,099 A | 3/1981 | Dryden | |
| 4,509,514 A | 4/1985 | Brain | |
| 4,553,540 A | 11/1985 | Straith | |
| 4,793,327 A | 12/1988 | Frankel | |
| 4,832,020 A | 5/1989 | Augustine | |
| 4,872,483 A | 10/1989 | Shah | |
| 4,953,547 A | 9/1990 | Poole, Jr. | |
| 4,995,388 A | 2/1991 | Brain | |
| 5,038,766 A | 8/1991 | Parker | |
| 5,042,469 A | 8/1991 | Augustine | |
| 5,203,320 A | 4/1993 | Augustine | |
| 5,235,973 A | 8/1993 | Levinson | |
| 5,241,956 A * | 9/1993 | Brain | 128/207.15 |
| 5,249,571 A | 10/1993 | Brain | |
| 5,277,178 A | 1/1994 | Dingley et al. | |
| 5,282,464 A * | 2/1994 | Brain | 128/207.15 |
| 5,297,547 A | 3/1994 | Brain | |
| 5,303,697 A | 4/1994 | Brain | |
| 5,305,743 A | 4/1994 | Brain | |
| 5,339,805 A | 8/1994 | Parker | |
| 5,339,808 A | 8/1994 | Don Michael | |
| 5,355,879 A | 10/1994 | Brain | |
| 5,391,248 A | 2/1995 | Brain | |
| 5,487,383 A | 1/1996 | Levinson | |
| 5,529,582 A | 6/1996 | Fukuhara | |
| 5,569,219 A | 10/1996 | Hakki et al. | |
| 5,582,167 A | 12/1996 | Joseph | |
| 5,584,290 A | 12/1996 | Brain | |
| 5,599,301 A | 2/1997 | Jacobs et al. | |
| 5,623,921 A | 4/1997 | Kinsinger et al. | |
| 5,632,271 A * | 5/1997 | Brain | 128/207.15 |
| RE35,531 E | 6/1997 | Callaghan et al. | |
| 5,653,229 A | 8/1997 | Greenberg | |
| 5,655,528 A | 8/1997 | Pagan | |
| 5,682,880 A | 11/1997 | Brain | |
| 5,694,929 A | 12/1997 | Christopher | |
| 5,711,293 A | 1/1998 | Brain | |
| 5,738,094 A | 4/1998 | Hoftman | |
| 5,743,254 A | 4/1998 | Parker | |
| 5,743,258 A | 4/1998 | Sato et al. | |
| 5,746,202 A | 5/1998 | Pagan | |
| 5,771,889 A | 6/1998 | Pagan | |
| 5,791,341 A | 8/1998 | Bullard | |
| 5,850,832 A | 12/1998 | Chu | |
| 5,865,176 A | 2/1999 | O'Neil | |
| 5,878,745 A * | 3/1999 | Brain | 128/207.15 |
| 5,881,726 A | 3/1999 | Neame | |
| 5,896,858 A | 4/1999 | Brain | |
| 5,915,383 A | 6/1999 | Pagan | |
| 5,937,860 A | 8/1999 | Cook | |
| 5,979,445 A | 11/1999 | Neame et al. | |
| 5,983,897 A | 11/1999 | Pagan | |
| 5,988,167 A | 11/1999 | Kamen | |
| 5,996,582 A | 12/1999 | Turnbull | |
| 6,003,510 A | 12/1999 | Anunta | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,070,581 A * | 6/2000 | Augustine et al. | 128/207.15 |
| 6,079,409 A * | 6/2000 | Brain | 128/200.26 |
| D429,811 S | 8/2000 | Bermudez et al. | |
| 6,095,144 A * | 8/2000 | Pagan | 128/207.15 |
| 6,116,243 A * | 9/2000 | Pagan | 128/207.15 |
| 6,119,695 A * | 9/2000 | Augustine et al. | 128/207.15 |
| 6,240,922 B1 | 6/2001 | Pagan | |
| 6,390,093 B1 | 5/2002 | Mongeon | |
| 6,427,686 B2 | 8/2002 | Augustine et al. | |
| 6,439,232 B1 * | 8/2002 | Brain | 128/207.15 |
| 6,631,720 B1 * | 10/2003 | Brain | 128/207.14 |
| 6,705,318 B1 | 3/2004 | Brain | |
| 7,004,169 B2 * | 2/2006 | Brain | 128/207.14 |
| 2003/0051734 A1 | 3/2003 | Brain | |
| 2003/0131845 A1 | 7/2003 | Lin | |

FOREIGN PATENT DOCUMENTS

| | | |
|---|---|---|
| CA | 2012750 | 8/1999 |
| EP | 0389272 | 9/1990 |
| EP | 0402872 | 12/1990 |
| EP | 0294200 | 4/1992 |
| EP | 0580385 | 5/1996 |
| EP | 0712638 | 5/1996 |
| EP | 0732116 A2 | 9/1996 |
| EP | 0796631 | 9/1997 |
| EP | 0845276 | 6/1998 |
| EP | 0865798 | 9/1998 |
| EP | 0922465 | 6/1999 |
| EP | 1125595 | 8/2001 |
| EP | 1119386 B1 | 9/2005 |
| GB | 2111394 | 7/1983 |
| GB | 2205499 | 1/1991 |
| GB | 2298797 A | 9/1996 |
| GB | 2317342 | 3/1998 |
| GB | 2317830 | 4/1998 |
| GB | 2318735 | 5/1998 |
| GB | 2319478 | 5/1998 |
| GB | 2321854 | 8/1998 |
| GB | 2323289 | 9/1998 |
| GB | 2323290 | 9/1998 |
| GB | 2323291 | 9/1998 |
| GB | 2323292 | 9/1998 |
| GB | 2359996 | 9/2001 |
| JP | 10118182 | 5/1998 |
| JP | 10216233 | 8/1998 |
| JP | 10263086 | 10/1998 |
| JP | 10277156 | 10/1998 |
| JP | 10314308 | 12/1998 |
| JP | 10323391 | 12/1998 |
| JP | 10328303 | 12/1998 |
| JP | 11128349 | 5/1999 |
| JP | 11192304 | 7/1999 |
| JP | 11206885 | 8/1999 |
| WO | WO-91/03207 | 3/1991 |
| WO | WO-91/07201 | 5/1991 |
| WO | WO-91/12845 | 9/1991 |
| WO | WO-92/13587 | 8/1992 |
| WO | WO-95/33506 | 12/1995 |
| WO | WO-97/12640 | 4/1997 |
| WO | WO-97/12641 | 4/1997 |
| WO | WO-98/16273 | 4/1998 |
| WO | WO-99/06093 | 2/1999 |
| WO | WO-00/09189 | 2/2000 |
| WO | WO-00/22985 | 4/2000 |
| WO | WO-00/23135 | 4/2000 |
| WO | WO-00/61212 | 10/2000 |

OTHER PUBLICATIONS

Benumof, "Laryngeal Mask Airway and the ASA Difficult Airway Algorithm," Anesthesiology, 1996, vol. 84(3), pp. 686-699.

Bernhard et al., "Adjustment of Intracuff Pressure to Prevent Aspiration," Anesthesiology, 1979, vol. 50(4), pp. 363-366.

Bernhard et al., "Physical Characteristics of and Rates of Nitrous Oxide Diffusion into Tracheal Tube Currs," Anesthesiology, 1978, vol. 48, pp. 413-414.

Brain, "The Laryngeal Mask—A New Concept in Airway Management," Br. J. Anaesth., 1983, vol. 55, pp. 801-805.

Brain, "The Laryngeal Mask Airway—A Possible New Solution to Airway Problems in the Emergency Situation," Archives of Emergency Medicine, 1984, vol. 1, pp. 229-232.

Brain, "The Laryngeal Mask Airway," Anaesthesia, 1985, vol. 40, pp. 356-361.

Brain, "Three Cases of Difficult Intuition Overcome by the Laryngeal Mask Airway," Anaesthesia, 1985, vol. 40, pp. 353-355.

Brain, et al., "A New Laryngeal Mask Prototype," Anaesthesia, 1995, vol. 50, pp. 42-48.

Brimacombe, "The Split Laryngeal Mask Airway," p. 639.

Broderick et al., "The Laryngeal Mask Airway," Anaesthesia, 1989, vol. 44, pp. 238-241.

Burgard, et al., "The Effect of Laryngeal Mask Cuff Pressure on Postoperative Sore Throat Incidence," J. Clinical Anesthesia, 1996, vol. 8, pp. 198-201.

Caplan et al., "Adverse Respiratory Events in Anesthesia: A Closed Claims Analysis", Anesthesiology, 72:828-833, 1990.

Communication of a notice of opposition, European Patent Office, Feb. 15, 2006 (cover page and pp. 1-4).

Craven, "Prevention of Hospital-Acquired Pneumonia: Measuring Effect in Ounces, Pounds, and Tons," Annals of Internal Medicine, 1995, vol. 122(3), pp. 229-231.

Cuff-Pressure-Control DCR, 2000, LogoMed.

Davies, et al., "Laryngeal Mask Airway and Tracheal Tube Insertion by Unskilled Personnel," The Lancet, vol. 336, pp. 977-979.

DeMello, et al., "The Use of the Laryngeal Mask Airway in Primary Anaesthesia," Anaesth. Corresp., 1990, vol. 45, pp. 793-794.

Doyle et al., "Intraoperative Awareness: A Continuing Clinical Problem," http://doyle.ibme.utoronoto.ca/anesthesia/aware.htm.

Engbers, "Practical Use of 'Diprifusor' Systems," Anaesthesia, 1998, vol. 53(1), pp. 28-34.

Eriksson et al., "Functional Assessment of the Pharynx at Rest and During Swallowing in Partially Paralyzed Humans," Anesthesiology, 1997, vol. 87(5), pp. 1035-1042.

Glen, "The Development of 'Diprifusor': A TCI System for Propofol," Anaesthesia, 1998, vol. 53(1), pp. 13-21.

Gray et al., "Development of the Technology for 'Diprifusor' TCI Systems," Anaesthesia, 1998, vol. 53(1), pp. 22-27.

Heath, "Endotracheal Intubation Through the Laryngeal Mask—Helpful When Laryngoscopy is Difficult or Dangerous," European J. of Anaesthesiology, 1991, vol. 4, pp. 41-45.

Hickey, et al., "Cardiovascular Response to Insertion of Brain's Laryngeal Mask," Anaesthesia, 1990, vol. 45, pp. 629-633.

Inomata et al., "Transient Bilateral Vocal Cord Paralysis After Insertion of a Laryngeal Mask Airway," Anesthesiology, 1995, vol. 82, pp. 787-788.

Jacobson et al., "A Study of Intracuff Pressure Measurements, Trends and Behaviours in Patients During Prolonged Period of Tracheal Intubation," Br. J. Anaesth., 1981, vol. 53, pp. 97.

Kambic et al., "Intubation Lesions of the Larynx," Br. J. Anasth. 1978, vol. 50, pp. 587-590.

Lindholm, "Prolonged Endotracheal Intubation," ACTA Anaesthesiologica Scandinavica, 1969, vol. 33, pp. 32-46.

Majumder et al., "Bilateral Lingual Nerve Injury Following the Use of the Laryngeal Mask Airway," Anaesthesia, 1998, vol. 53, pp. 184-186.

Miller, "A Pressure Regulator for the Cuff of a Tracheal Tube," Anaesthesia, 1992, vol. 47, pp. 594-596.

Muthuswamy et al., "The Use of Fuzzy Integrals and Bispectral Analysis of the Electroencephalogram to Predict Movement under Anesthesia," IEEE Transactions on Biomedical Engineering, 1999, vol. 46(3), pp. 290-299.

Nagai, "Unilateral Hypoglossal Nerve Paralysis Following the Use of the Laryngeal Mask Airway," Anaesthesia, 1994, vol. 49, pp. 603-604.

Observations by Third Party Concerning European Patent Application No. 99 947 765.6-2318, European Patent Office, Munich, Germany, Jan. 18, 2005 (3 pgs.).

Patel et al., "Tracheal Tube Cuff Pressure," Anaesthesia, 1984, vol. 39, pp. 862-864.

Pennant, "Comparison of the Endotracheal Tube and Laryngeal Mask in Airway Managemet by Paramedical Personnel," Anesth. Analg., 1992, vol. 74, pp. 531-534.

Pippin et al., "Long-Term Tracheal Intubation Practice in the United Kingdom," Anaesthesia, 1983, vol. 38, pp. 791-795.

Raeder et al. "Tracheal Tube Cuff Pressures," Anaesthesia, 1985, vol. 40, pp. 444-447.

Response to Complaint Matter No. 4b 0 440-05, In the Matter of: LMA Deutschland GmbH versus Ambu (Deutschland) GmbH, Feb. 10, 2006, pp. 1-47.

Seegobin et al., "Endotracheal Cuff Pressure and Tracheal Mucosal Blood Flow: Endoscopic Study of Effects of Four Large Volume Cuffs," British Medical Journal, 1984, vol. 288.

Willis et al., "Tracheal Tube Cuff Pressure," Anaesthesia, 1988, vol. 43, pp. 312-314.

Worthington, et al., "Proceedings of the Anaesthetic Research Society," Br. J. Anaesthesia, 1995, vol. 75, pp. 228P-229P.

Wynn et al., "Tongue Cyanosis After Laryngeal Mask Airway Insertion," Anesthesiology, 1994, vol. 80(6), pp. 1403.

* cited by examiner

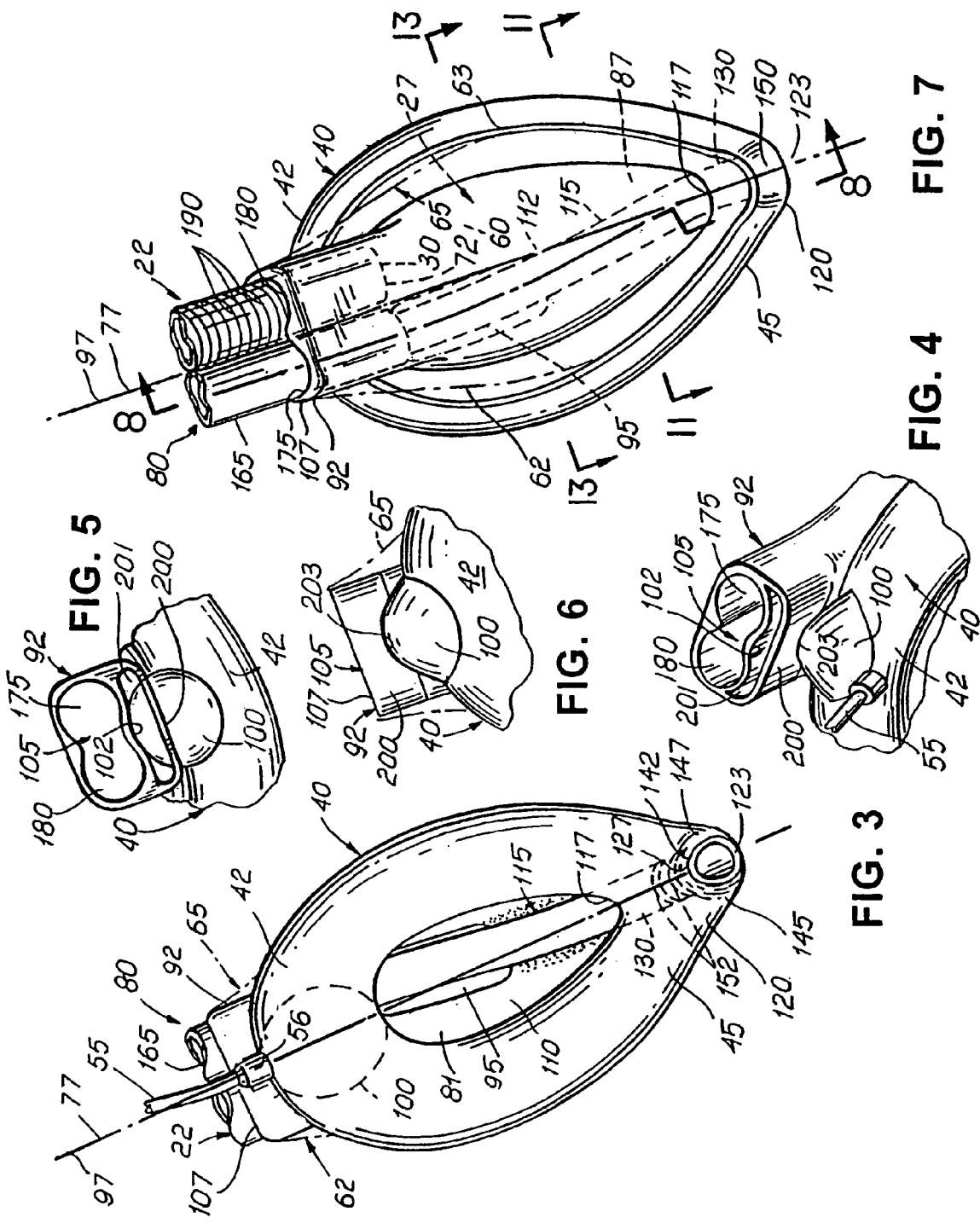

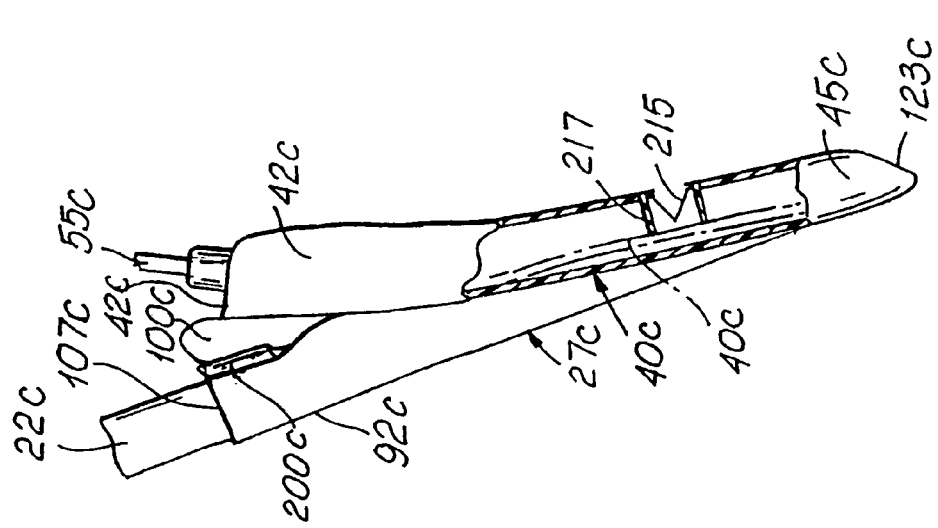
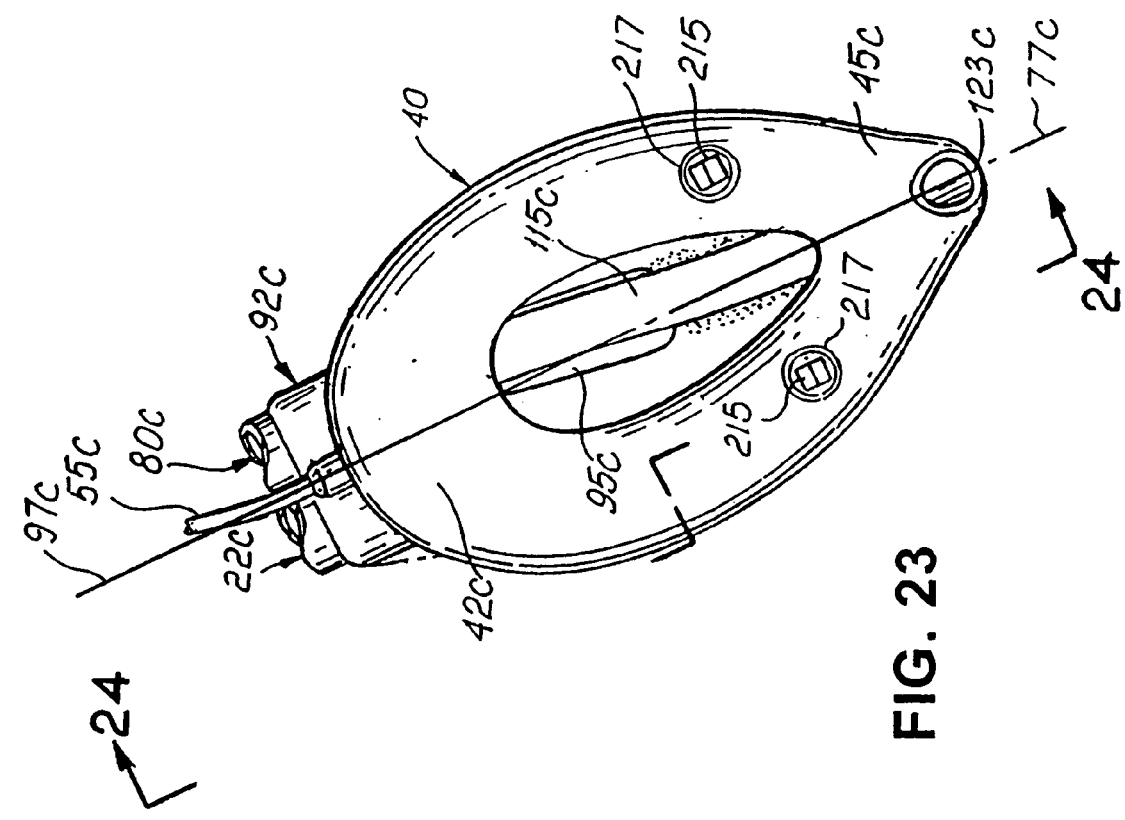

LARYNGEAL MASK AIRWAY DEVICE

CROSS-REFERENCE SECTION

This application is a continuation of U.S. patent application Ser. No. 10/225,678, filed Aug. 22, 2002, now abandoned, which is a continuation of U.S. patent application Ser. No. 09/289,319, filed Apr. 9, 1999, now U.S. Pat. No. 6,439,232. This application also claims the benefit of United Kingdom patent application 9716537.5 filed Aug. 13, 1998.

BACKGROUND OF THE INVENTION

This invention relates to laryngeal mask airway devices (LMA-devices). Such devices are useful in facilitating lung ventilation in unconscious patients by forming a low pressure seal around the patient's laryngeal inlet, avoiding the known harmful effects of the endotracheal tube, which forms a seal within the windpipe (trachea).

LMA-devices of the types disclosed in UK Patent Nos. 2111394 and 2205499 have become accepted items of equipment for rapidly and reliably establishing an unobstructed airway in a patient in emergency situations and in the administration of anaesthetic gases, and have found use in most countries of the world. A disadvantage associated with the use of such a mask is encountered in a patient who is at risk from vomiting or regurgitating stomach contents while unconscious since although the device forms a seal around the laryngeal inlet sufficient to permit artificial ventilation of the lungs, the seal is sometimes insufficient to prevent lung contamination during retching, vomiting or regurgitation.

A partial solution to this problem is disclosed in U.S. Pat. No. 4,995,388 in which reliance is made upon a combination of an improved peripheral continuity of seal pressure against the laryngeal inlet and the provision of a drainage tube to conduct gastric contents away from the laryngeal inlet. However, one embodiment of such a system is itself disadvantaged by the fact that the removal of such gastric discharges can be achieved only after the seal between the LMA device and the laryngeal inlet/oesophagus has been breached. Another embodiment provides for removal of gastric drainage without breaching the seal between the LMA device and laryngeal inlet/oesophagus, but this proved awkward to insert and caused throat irritation.

A more successful solution to this problem has been provided by the gastro-laryngeal mask airway device disclosed in U.S. Pat. No. 5,241,956 and European Patent 651664. In that device, a drainage tube passes through the posterior aspect of the mask and through the distal end of the inflatable cuff of the mask to open in alignment with the patient's oesophagus. However, the drainage tube must be sufficiently rigid at its distal end to withstand the pressure within the inflated cuff and it has been found that this may make proper insertion of the deflated device into the patient's throat more difficult than either necessary or desirable.

In a modified gastro-laryngeal mask airway device disclosed in International Patent Application WO 97/12680, provision is made for the distal half of the mask to be of softly compliant construction, and to ensure against collapse of the drainage tube when the cuff is inflated. Also, the mask has a flexible leading edge for facilitating correct insertion into the throat of the patient.

European Patent Application 796631 and U.S. Pat. No. 5,632,271 disclose an LMA device which further facilitates insertion into the throat of the patient, an LMA device includes a drainage tube, which opens into the distal tip of the mask, passes along the posterior aspect of the flexible airway tube and emerges from the mouth of the patient just below the upper incisor teeth. For practical purposes this device works well but has the following limitations.

A disadvantage of this back-to-back tube orientation is that it confers a degree of instability to the mask when the device is in place, permitting the possibility of loss of seal between the mask and laryngeal inlet. Another disadvantage of the back-to-back tube configuration is that it confers to the tubular elements of the device an undesirable degree of stiffness so that movements of the head and neck of the patient occasioned, for example, by surgical manipulation or positioning, may result in undue harmful pressure being exerted on the surrounding tissues of the upper airway passages.

Another disadvantage is that the inserting index finger tends to slip off the airway and drainage tube due to lack of purchase. A still further disadvantage is that the inserting index finger may be damaged by the teeth of the patient because of the greater combined diameter of the back-to-back tubes.

SUMMARY OF THE INVENTION

The present invention has as its overall objective to provide an LMA device of the types described above, i.e., incorporating means for draining gastric discharge from the region of the oesophageal inlet of the patient, which substantially avoids the disadvantages described above in relation to various of the known types of LMA-devices.

In accordance with the invention, this objective is achieved by first modifying the bowl of the mask such that its interior curvature has a significantly deeper shape than previous constructions. This is accomplished by either making the posterior wall or backplate of the mask to generally the same peripheral dimensions to permit its attachment to the posterior aspect of the inflatable cuff formation (in contrast to attachment to the inner rim or equator of the cuff formation), or by changing the cross section shape of the cuff so that its seam is placed at offset from the major or equatorial plane. Hence, the backplate is located substantially behind, i.e., posteriorly of the cuff and not, as previously, within the annulus of the cuff. The backplate edge, or rim, is attached roughly tangentially with respect to the roughly ring-shaped cross-section of the inflatable toroidal shape of the cuff annulus. It will be evident that with this construction, the depth of the bowl of the mask, i.e., the distance between the anterior aspect of the cuff when inflated and the anterior aspect of the backplate, will be greater than in previous constructions by approximately half the posterior-anterior dimension of the inflated cuff. Since most adult-size LMA devices have cuff inflation diameters in the range of 12 to 16 millimeters, it is clear that the additional bowl depth will be of the order of 6 to 8 millimeters. This additional bowl depth permits the gastric drain tube to be on the anterior surface of the backplate instead of running posteriorly as in previous designs, increasing the stability of the mask when installed in the throat of the patient and reducing the tendency of the installed device to migrate outwardly.

This anterior placement of the drain tube also eliminates the requirement to guard the aperture of the airway tube against obstruction by the anatomical structure known as the epiglottis. To prevent such obstruction, former cuffs were provided with paired parallel bars running across the airway aperture. These bars proved effective in preventing epiglottis obstruction but offered unwanted resistance to airflow and tended to obstruct passage of suction or inspection tubing. Anterior positioning of the drain tube allows it to act as an epiglottic prop, holding back the epiglottic rim from the floor of the mask and the airway port. The paired bars described above were not able to prevent obstruction occurring as a result of the epiglottic rim lying in contact with the bowl or floor of the mask. The anterior location of the drain tube in the present invention overcomes the problems of epiglottic misplacement more effectively than the previous design.

The second modification to the backplate is to replace the single tube-joint port adapted to accept the flexible airway tube with a double-barrelled port in which said ports are arranged side-by-side, that is to say laterally, permitting easy assembly of said side-by-side airway and drainage tubes. This provides better correspondence with the cross section space within the throat, the major axis of which runs laterally, and reduces stiffness and consequent pressure on the throat from movements of the head and neck of the patient. Also, the side-by-side adjacency reduces the pressure exerted on the drainage tube by the incisor teeth of the patient, and facilitates manufacturing since the portions of the tubes in the throat of the patient describe similar radii.

The double-barrelled tube-joint additionally provides a desirable locating point for the tip of the index finger used to insert the device, thus reducing possible slipping of the finger on the tube-joint. Also, the reduced transverse diameter in the vertical direction between the teeth of the patient resulting from the side-by-side adjacency of the drainage and airway tubes reduces possible injury to the finger from contact with the teeth.

A third modification to the backplate is the incorporation of a well or depression covering an area of approximately 3 square centimeters and having a 2 to 5 millimeters depth situated in the anterior surface of the backplate under the drain tube where it connects with the distal end of the drain port of the backplate. The well has the dual functions of permitting gas circulation and allowing secretions from the trachea to be drained away.

The LMA device of the invention is readily distinguished from the devices proposed hitherto in which the backplate of the mask has been located within the annulus of the inflatable cuff, and in which the gastric drainage tube has been routed across the posterior surface of the backplate.

According to the invention, therefore, there is provided a laryngeal mask airway device equipped for drainage of gastric discharge, the device comprising an inflatable main-cuff and a backplate having a laryngeal-side and a pharyngeal-side. The backplate also has an external tube-joint adjacent to the proximal end of the main-cuff. The backplate is hermetically bonded to the periphery of the main-cuff establishing separation between a laryngeal-chamber region and a pharyngeal region. A distally open evacuation tube includes a distal portion which longitudinally traverses the interior of the distal region of the main-cuff in sealed relation therewith for operative engagement and communication with the inlet of the oesophagus. The evacuation tube traverses the laryngeal-chamber region generally adjacent to the laryngeal-side of the backplate and passages through a proximally located tube-joint to the pharyngeal region. An airway tube also extends into the tube-joint for communication with an airway port to provide a flowpath between the airway tube and laryngeal-chamber region.

These and other objects, features, and advantages of the invention will be more fully understood from the following description of certain specific embodiments of the invention taken together with the accompanying drawings.

BRIEF DESCRIPTION OF THE DRAWINGS

In the drawings:

FIG. 3 is a plan view of the anterior side of the LMA-device of FIG. 1, the main-cuff being inflated and illustrated in enlarged scale relative to FIG. 1, the airway and external-drain tubes being cut-off, the well hidden behind the internal-drain tube also being shown;

FIG. 4 is an enlarged perspective view of a detail of FIG. 3 with the airway and evacuation tubes removed, showing the anterior surface of the tube-joint and the posterior bulge of the main-cuff;

FIG. 5 is an enlarged plan view of a detail of FIG. 3 with the airway and evacuation tubes removed, showing the anterior surface of the tube-joint and the posterior bulge of the main-cuff;

FIG. 6 is an enlarged end view of a detail of FIG. 3 with the airway and evacuation tubes removed, showing the proximal end surface of the tube-joint and the posterior bulge of the main-cuff;

FIG. 7 is a plan view of the posterior side of the device of FIG. 1, in the same inflated condition as and to the scale of FIG. 3, the portions of the airway tube and the external- and internal-drain tubes hidden in the tube-joint being shown, the well hidden behind the backplate also being shown;

FIG. 23 is a plan view of the anterior side of a third embodiment of the LMA-device of FIGS. 3 and 7 showing one-way valves incorporated in the anterior wall of the main-cuff; and FIG. 24 is a lateral view of the main-cuff of the embodiment illustrated in FIG. 23 in the direction indicated by line 23-23 showing one of the one-way valves and its associated housing.

Corresponding reference characters indicate corresponding parts throughout the several views of the drawings.

DETAILED DESCRIPTION OF THE INVENTION

As used herein, the anatomical terms "anterior" and "posterior", with respect to the human body, refer to locations nearer to the front of and to the back of the body, respectively, relative to other locations. The term "anterior-posterior (A-P)" refers to a direction, orientation or the like pointing either anteriorly or posteriorly. The anatomical terms "proximal" and "distal", with respect to applying an instrument to the human body, refer to locations nearer to the operator and to the inside of the body, respectively. Alternatively, "distal", as opposed to "proximal", means further away from a given point; in this case, "distal" is used to refer to positions on the LMA-device 20 or in the body relative to the extreme outer or connector end of the LMA-device. "Proximal" is the opposite of "distal". The term "lateral" refers to a location to the right or left sides of the body, relative to other locations. Alternatively, "lateral" means to one or other side of the mid-line, with respect to the major axis of the body, or to a device lying in the body's major axis. The term "bilateral" refers to locations both to the left and right of the body, relative to the sagittal plane. The term "sagittal" or "sagittally" refers to a vertical longitudinal plane through the center or midline of the body that divides a bilaterally symmetrical body into right and left halves. The sagittal plane is the plane passing antero-posteriorly through the middle of the body in its major axis. The term "medial" means nearer to the mid-line.

Figure 1:
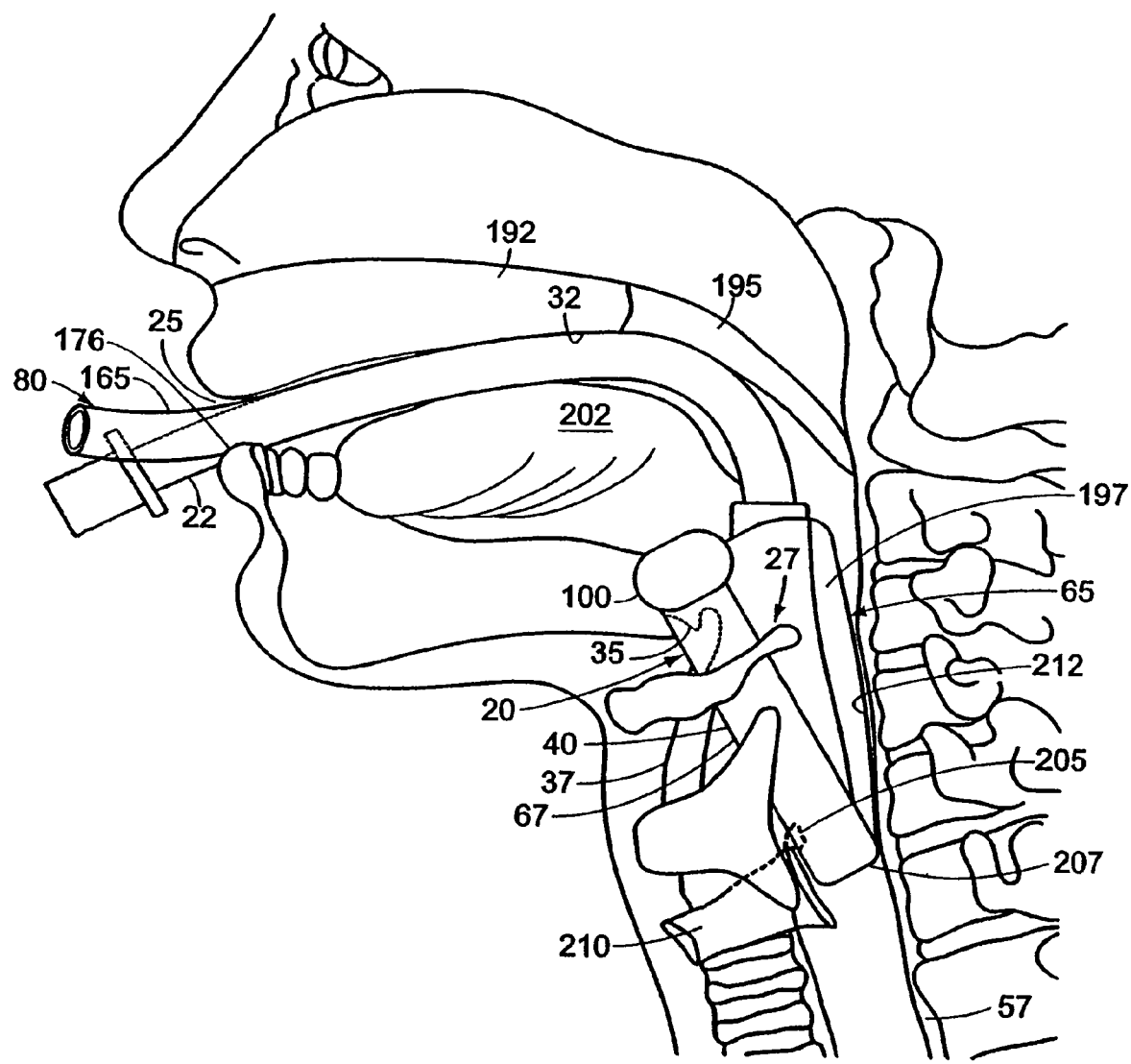
FIG. 1 is a simplified overall view to show an LMA-device of the invention, installed in a patient whose relevant anatomical features are shown by phantom outlines.
Figure 2:
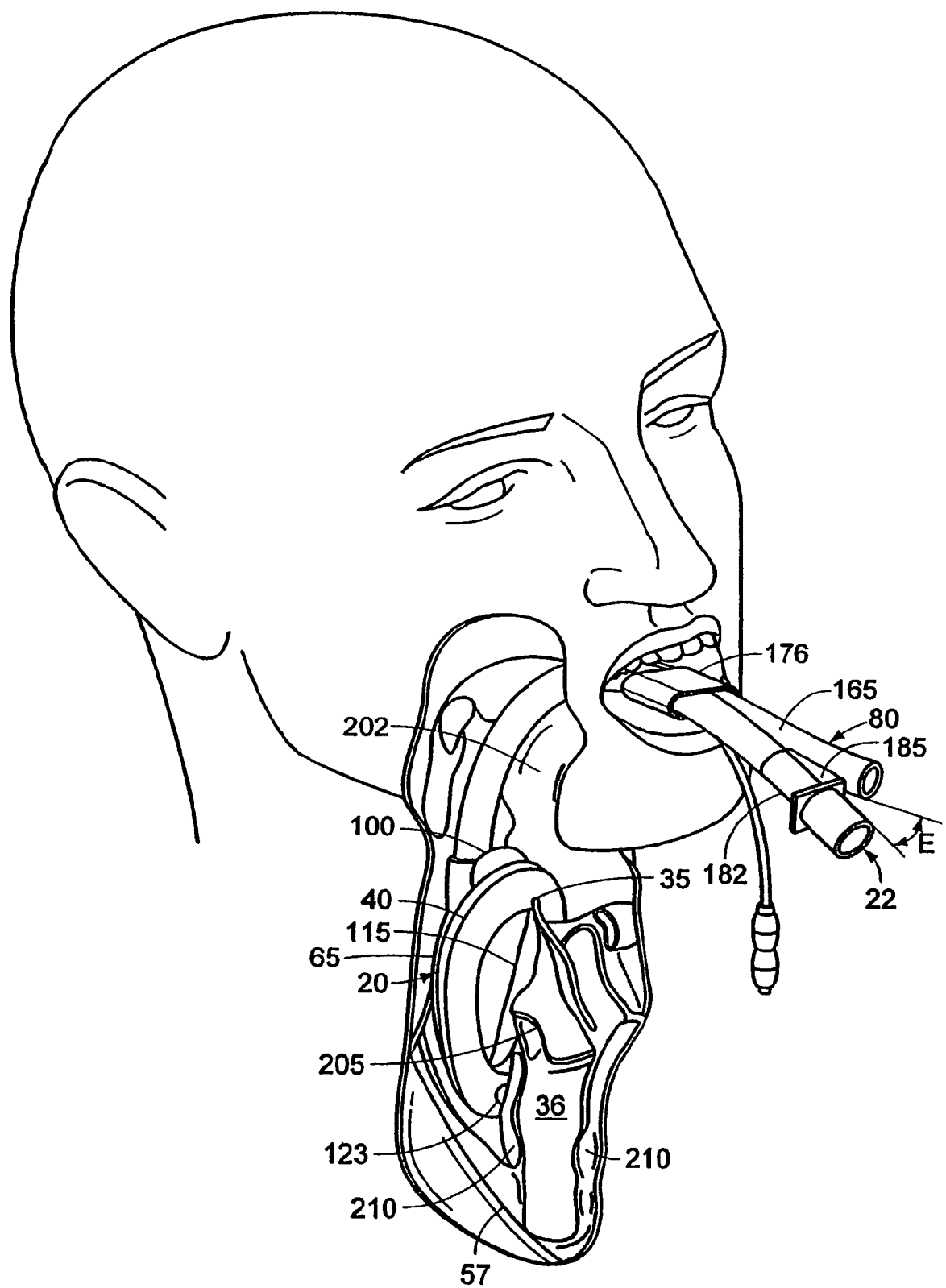
FIG. 2 is a perspective view showing the LMA-device of FIG. 1 installed in a patient, the patient being shown in the quarter neck direction from the front right-side omitting most neck structures and showing a sagittal section of the larynx, the epiglottis being shown displaced anteriorly relative to the main-cuff to show the internal-drain tube (normally, the epiglottis extends into the main-cuff), the right lateral portion and proximal region, including the hemispherical posterior bulge, of the main-cuff being shown.

A laryngeal-mask airway device (LMA-device) of the present invention, is designated generally by the reference numeral 20 in FIGS. 1 and 2. The LMA-device 20, in a deflated condition, is inserted into the throat 32 the upper surface of which is bounded by hard and soft palates 192, 195. The LMA-device 20 is lodged in the pharynx 197 of the throat 32 at the base of the hypo-pharynx 212 where the throat divides into the trachea 36 (i.e., windpipe) and oesophagus 57. A lower portion of the LMA-device 20 reaches to the base of the hypo-pharynx 212. After the LMA-device 20 is so lodged in the pharynx 197 such that the lower portion of the LMA-device reaches the base of the hypo-pharynx 212, the LMA-device is inflated. Disposed in the junction between the throat 32 and trachea 36 is the flexible epiglottis 35 (i.e., a lid-shaped structure) which forms the upper border of the larynx 37, entry through which is provided by the laryngeal inlet 67. To facilitate understanding of the relations between the LMA-device 20 and anatomy of the throat 32 and related structures, a glossary of the anatomical structures related to the LMA-device is provided herein below.

Referring to FIGS. 1 and 2, the laryngeal-mask airway device (LMA-device) 20 is shown comprising an airway tube 22, installed through the mouth 25 of a patient. The LMA-device 20 further comprises a backplate 27 having an airway port 30 through which the airway tube 22 can establish a free externally accessible ventilation passage, via the patient's mouth 25 and throat 32, and past the epiglottis 35 to the larynx 37. The backplate 27 is preferably of an elastomer such as silicone rubber and relatively stiff, for example, of 80 Shore durometer.

As further shown in FIGS. 3 and 7, the backplate 27 is surrounded by a main-cuff 40 comprising an inflatable ring which, when inflated, has the shape of a torus generated by an asymmetrical oval or ellipse having a wider proximal region 42 and narrower distal region 45. The main-cuff 40 is circumferentially united to the backplate 27 in essentially a single plane, except for the portion of the main-cuff extending into a recess 47 in a heel 50 of the backplate 27. The portion of the main-cuff 40 extending into the recess 47 may or may not be united to the backplate 27, as described further hereinbelow.

The main-cuff 40 may also be of silicone rubber, although preferably relatively soft and flexible compared to the backplate 27. The material of the main-cuff 40 is preferably of 20 to 30 Shore durometer. Except for a plastic connector (not shown) attached to the proximal end of the airway tube 22 and a check valve 52, all parts of the LMA-device 20 disclosed herein are preferably made of silicone, possibly with different additives.

An externally accessible tube 55 and inflation port 56 on the main-cuff 40 are the means of supplying air to the main-cuff and of extracting air from (and therefore collapsing) the main-cuff for purposes of insertion in or removal from the patient. The check-valve 52 is disposed in the tube 55 for holding a given inflation or holding a given deflation of the main-cuff 40.

Figure 11:
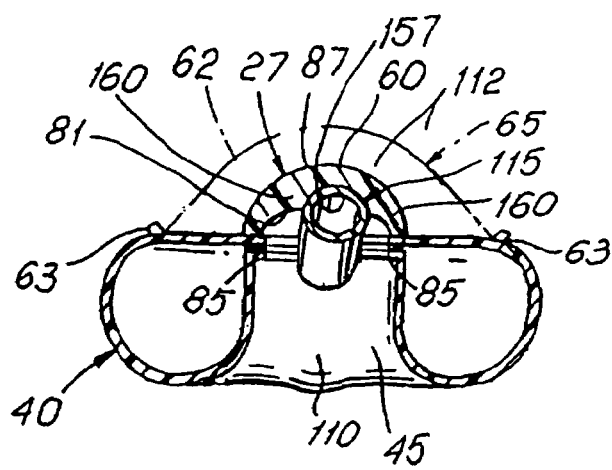
FIG. 11 is a distal view in cross section, in the plane indicated by the line 11-11 of FIG. 7 showing the engagement between the internal-drain tube and backplate, and the adjacency between the seam in the main-cuff and backplate.
Figure 13:
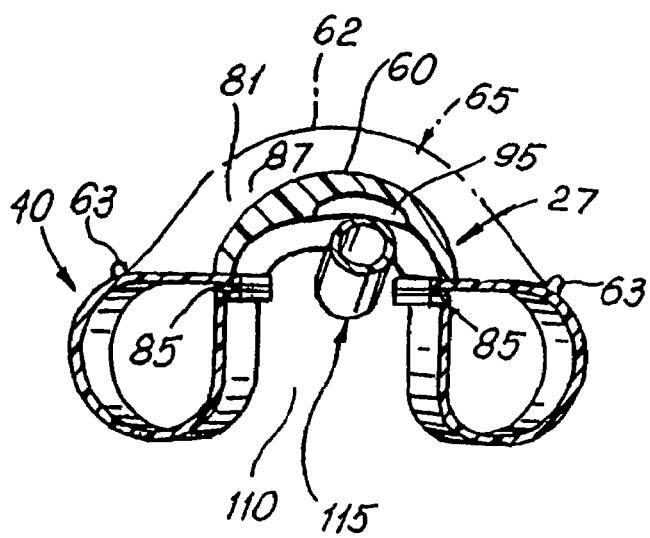
FIG. 13 is a distal view in cross section, in the plane indicated by the line 13-13 of FIG. 7 showing a portion of the LMA-device between lines 11-11 and 13-13, the clearance between the internal-drain tube and base of the well being illustrated.

In the installed position of FIGS. 1 and 2, the projecting but blunted distal region 45 of the main-cuff 40 is shaped to conform with the base of the hypo-pharynx 212 where it has established limited entry into the upper sphincteral region of the oesophagus 57. The pharyngeal-side 60 of the backplate 27 is covered by a thin flexible panel 62, as shown in FIGS. 7, 11 and 13, which is peripherally bonded to a margin 63 on the posterior surface of the main-cuff 40, to define an inflatable back-cuff 65 comprising a cushion which assures referencing to the posterior wall of the pharynx and thus is able to load the inflated main-cuff forward for enhanced effectiveness of sealing engagement to the inlet 67 of the larynx 37. The inflated main-cuff 40, thus-engaged to the laryngeal inlet 67, orients a distal-end 72 of the airway tube 22 at an acute angle to a mid-line major plane 75 of the main-cuff 40 and in substantial alignment with the axis of the laryngeal inlet 67, for direct airway communication only with the larynx 37.

The major plane 75 is a plane containing the major axis 77 of main-cuff 40 extending between proximal and distal regions 42, 45. The major plane 75 is disposed between, and parallel to, the anterior and posterior surfaces of the main-cuff 40. Additionally, the major plane 75 is equidistant from the anterior and posterior surfaces of the main-cuff 40, except for posterior bulge 100.

The LMA-device 20 is of the GLM (gastro-laryngeal mask) variety in which an evacuation tube, designated generally by 80, as shown in FIGS. 1, 2, 3 and 7, serves for extraction and external removal of gastric-discharge products from the oesophagus 57. Additionally, the evacuation tube 80 provides a pathway into the oesophagus 57 for insertion, for example, of a gastric feeding tube, suction catheter, temperature probe or other monitoring device, probes carrying stimulating electrodes such as pacing wires, sengstaken balloons, or other catheters bearing inflatable cuffs, fiber optic endoscopes or medication. The evacuation tube 80 follows the general course of the airway tube 22, with sealed entry through the backplate 27 alongside the airway tube, on the laryngeal-side 81 of the backplate, and with sealed passage through the interior of the main-cuff 40 and open through the distal region 45 of the main-cuff. Inflation-air supply to the back-cuff 65 may be via the same tube 55 as for the main-cuff 40, or separate inflating means (not shown) may be provided for the back-cuff 65. The disclosures of U.S. Pat. Nos. 5,241,956, and 5,632,271, and 5,878,745 disclosing various laryngeal mask devices, are hereby incorporated by reference herein.

More specifically, the toroidal-shaped main-cuff 40 is formed by first moulding it in an intermediate stage having opposing edges, each of which has an elliptical shape. The opposing edges of the main-cuff 40, when in generally edge-to-edge relation, are welded together to form a seam 85, as shown in FIGS. 5, 11 and 13. The seam 85 defines an oval contained in a plane which is parallel to the major plane 75, corresponding to the internal surface of the main-cuff 40. When the backplate 27 is attached to the main-cuff 40, the seam 85 abuts the periphery of the oval portion 87 in anterior relation to the backplate, as best shown in FIGS. 11 and 13. The seam 85 may be inserted in a corresponding groove in the oval portion 87. Alternatively, the backplate 27 and main-cuff 40 may be extruded as a single, unitary piece.

As used herein, the term "welding" describes the bonding together of two components having the same or similar chemical compositions, either by adhesive having the same or similar chemical composition as the components, or by high pressure or temperature fusion, or a combination of any of them.

A separate tube (not shown), preferably with multiple perforations along its length, may be contained within the main-cuff 40 between the opening of the tube 55 into the main-cuff such that each perforation communicates with a port between the interiors of the main-cuff and back-cuff 65. Such a separate tube preserves a flowpath between the tube 55 and back-cuff 65 if the main-cuff 40 is completely collapsed from deflation, thereby providing for further deflation of the back-cuff 65 via the tube 55. Alternatively, a channel (not shown) may be formed on the inner surface of the main-cuff 40 between the opening of the tube 55 into the main-cuff and at least one of the one or more ports between the interiors of the main-cuff and back-cuff 65. Such a channel preserves a flowpath between the tube 55 and back-cuff 65 if the main-cuff 40 is completely collapsed from deflation.

The backplate 27 has a one-piece, integral spoon-shape which, with the oval portion 87, also has an external tube-joint 92. The tube-joint 92 is oriented proximally relative to the oval portion 87. Opposite sides of the oval portion 87 are defined by a convex pharyngeal-side 60 and concave laryngeal-side 81. The periphery of the oval portion 87 is hermetically bonded to the periphery of the main-cuff 40 to establish separation between the laryngeal-chamber region 110 and pharyngeal region 112.

Figure 10:
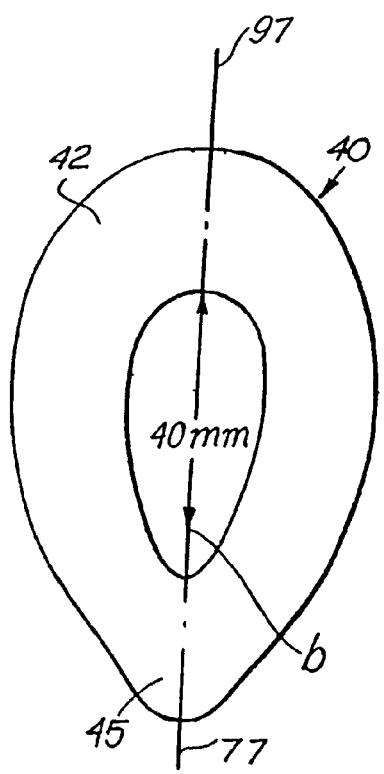
FIG. 10 is a sectional plan view in the plane indicated by the line 10-10 of FIG. 9 showing the location of the anterior-posterior dimension of FIG. 9 relative to the proximal region of the main-cuff.
Figure 12:
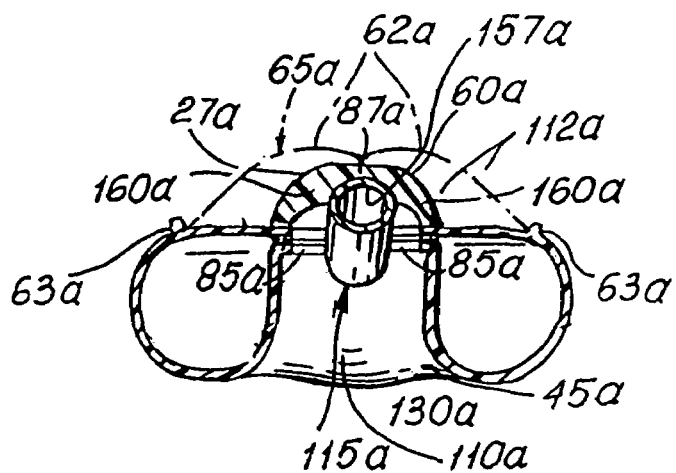
FIG. 12 is a distal view in cross-section of a second embodiment of the backplate and back-cuff in a plane corresponding to the plane indicated by line 11-11 of FIG. 7, showing a reduced wall thickness of the backplate in the sagittal plane, and the back-cuff tethered to the backplate.

The periphery of the oval portion 87 of the backplate 27 abuts, in proximal relation to, the seam 85 of the main-cuff 40 in its inflated condition, as shown in FIGS. 10 and 12. This more posterior location of the backplate 27, as compared to locating the periphery of the oval portion 87 in the major plane 75, provides additional space for the internal-drain tube 115. The oval portion 87 may be located at various positions in the anterior-posterior direction relative to the main-cuff 40 because of the generally constant cross-section of the laryngeal-chamber region 110 in planes parallel to major plane 75, as shown in FIGS. 10 and 12.

Formed in the laryngeal-side 81 is a well 95 defined by a depression adjacent to the tube-joint 92. The well 95 faces the evacuation tube 80 such that the well is offset relative to the sagittal plane 97 of the main-cuff 40. The well 95 thereby provides a radial clearance between the evacuation tube 80 and laryngeal-side 81.

Figure 8:
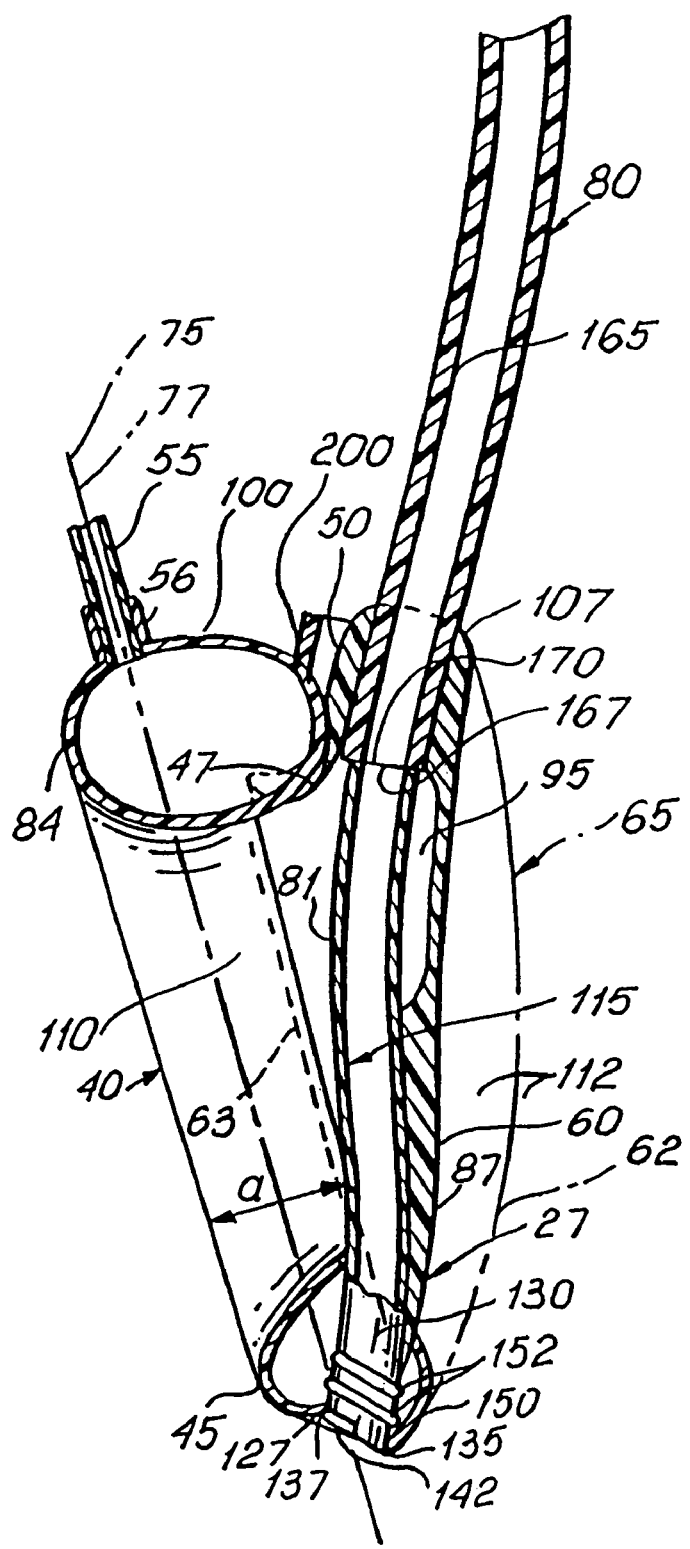
FIG. 8 is a lateral view in partial section, in the plane indicated by the line 8-8 of FIG. 7 which is parallel to the sagittal plane and which coincides with the central longitudinal axis of the evacuation tube, except in the distal region of the main-cuff where the evacuation tube is transversely offset from the sagittal plane, showing the longitudinal traverse of the internal-drain tube along the backplate.

The portions of the laryngeal-side 81 which are proximal and distal of the well 95 are inclined relative to the base of the well such that the laryngeal-side ramps anteriorly as it approaches the well in the distal and proximal directions, as shown in FIG. 8.

Figure 16:
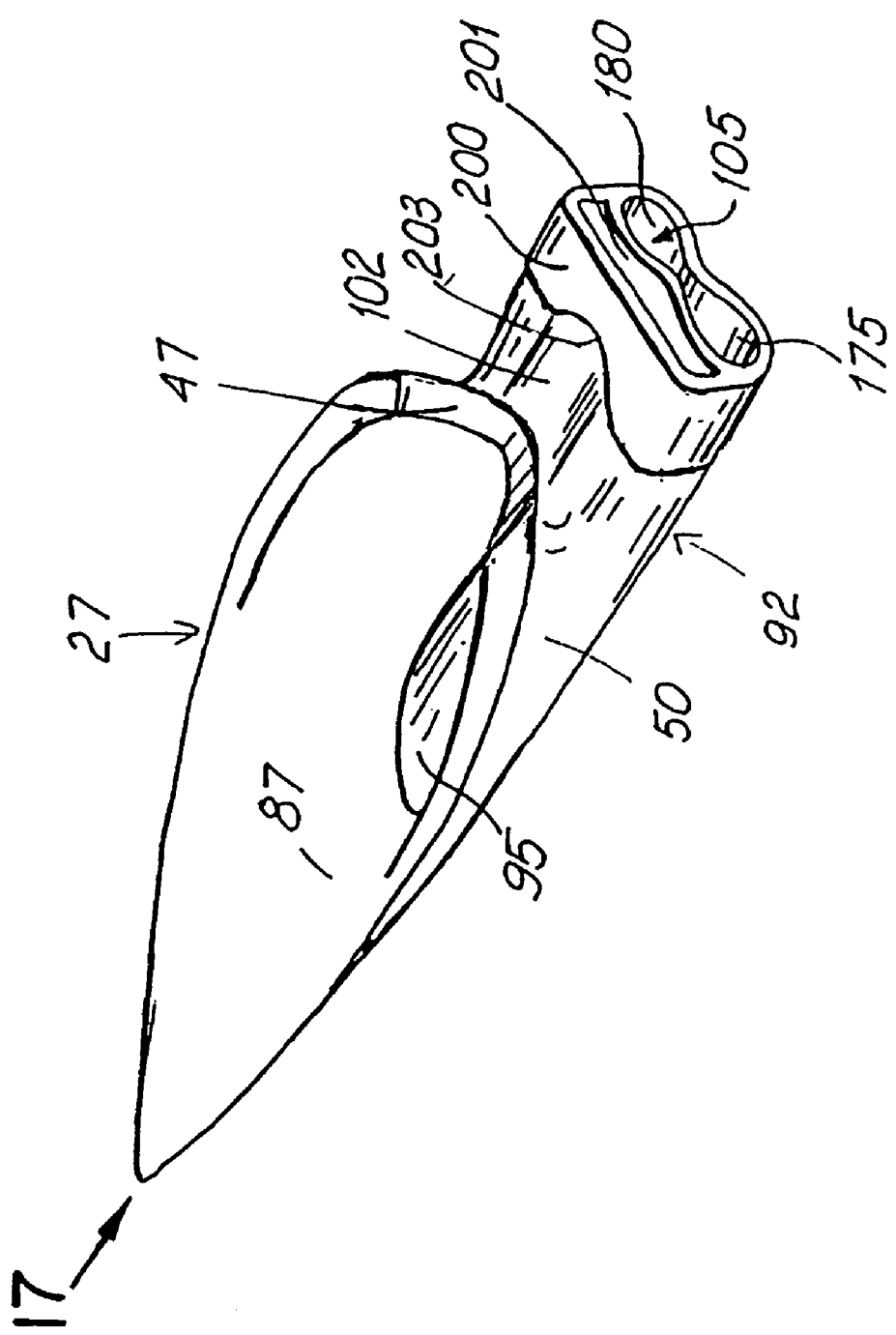
FIG. 16 is an anterior perspective view of the backplate removed from the LMA-device of FIGS. 3 and 7.

The periphery of the oval portion 87 adjacent to the tube-joint 92 is included in the heel 50. A portion of the heel 50 contiguous with its anterior edge is removed to define a crescent-shaped recess 47. The proximal region 42 of the main-cuff 40 has an approximately hemispherical posterior bulge 100 arising from its posterior surface, as shown in FIG. 8. The posterior bulge 100 extends posteriority symmetrically relative to the sagittal plane 97 to fit into the mid-line groove 102 forming part of the anterior surface of the double-barrelled tube-joint 92 of the backplate 27. The mid-line groove 102 is shown in FIG. 16. The posterior bulge 100 also extends into the crescent-shaped recess 47 to compensate for the reduced support provided by the backplate 27 resulting from the recess 47.

Less than the entire width of the main-cuff 40 extends posteriorly from the proximal region 42 because the recess 47 of the backplate 27 allows space for the main-cuff 40 to extend posteriorly in the approximately hemispherical posterior bulge 100. The posterior bulge 100 is partially supported bilaterally by the backplate 27 thus preventing ballooning-out of this portion of the main-cuff 40. Such ballooning-out of the main-cuff 40 would result in the flow of internal gases from other interior regions of the main-cuff resulting from redistribution of the pressure in the main-cuff, thereby resulting in an uneven seal between the main-cuff and the tissues surrounding the laryngeal inlet 67. Such an uneven seal might result in loss of seal, particularly at the pointed distal end of the main-cuff 40.

The recess 47 and mid-line groove 102 together form a partial socket which provides mechanical support posteriority, bilaterally and distally for the posterior bulge 100.

The posterior bulge 100 may be separable from the recess 47 to define a normally closed and therefore self-sealing port for insertion of an elongate member such as a probe, endotracheal tube, endoscope or the like from the pharyngeal-region 112 into the laryngeal-chamber region 110. This enables such-an elongate member to be inserted into the laryngeal-chamber region 110 without occupying the interior of the airway tube 22 which may obstruct air flow through the airway tube. Additionally, throughout insertion of such an elongate member through the port and the laryngeal-chamber region 110, the elongate member is anterior of the internal-drain tube 115.

In comparison, if such an elongate member is inserted through the airway port 30 into the laryngeal-chamber region 110, upon entry into the laryngeal-chamber region, the distal end of the elongate member lies substantially parallel to the internal-drain tube 115. Accordingly, shortly after entry into the laryngeal-chamber region 110, upon continued insertion into the laryngeal-chamber region, the insertion direction of such an elongate member must normally be sharply changed to enable entry into or viewing of the larynx 37 or bronchial tree. Additionally, insertion of such an elongate member through the airway port 30 into the laryngeal-chamber region 110 results in the elongate member being laterally offset from the sagittal plane 97 since the airway port is so offset from the sagittal plane. Such an elongate member must therefore be suitably steered if it is to be aligned in the sagittal plane 97. Aligning such an elongate member in the sagittal plane 97 may facilitate its further insertion through the larynx 37 into the trachea.

The elongate tube-joint 92 is formed on the pharyngeal-side 60 and extends posteriorly and proximally relative to the oval portion 87. The tube-joint 92 includes a longitudinal passageway 105 extending from its proximal end 107 distally to the concave laryngeal-side 81. The passageway 105 has a double-barrelled cross section for supporting the airway tube 22 and evacuation tube 80, described more fully herein below. The longitudinal central axis of the passageway 105 is contained in the sagittal plane 97 and inclined posteriority at an angle of approximately 30 degrees relative to the major plane 75, as viewed in the sagittal plane 97.

A strap 200 is moulded to the external anterior surface of the proximal tube-joint 92 in arching relation over the mid-line groove 102. The moulding of the strap 200 onto the anterior surface of the proximal portion of the tube-joint 92 defines an introducer tool slot 201. The distal edge of the strap 200 has an internal curved edge 203 against which abuts the posterior bulge 100 (which is an extension of the main cuff 40), as shown in FIGS. 4, 6 and 16. The introducer tool slot 201 and curved edge 203 avoid becoming dirt trap because when the main-cuff 40 is deflated, the posterior bulge 100 (i.e, the main-cuff extension) pulls away from the strap 200, thus avoiding the formation of a blind pocket which could be a dirt trap.

Figure 18:
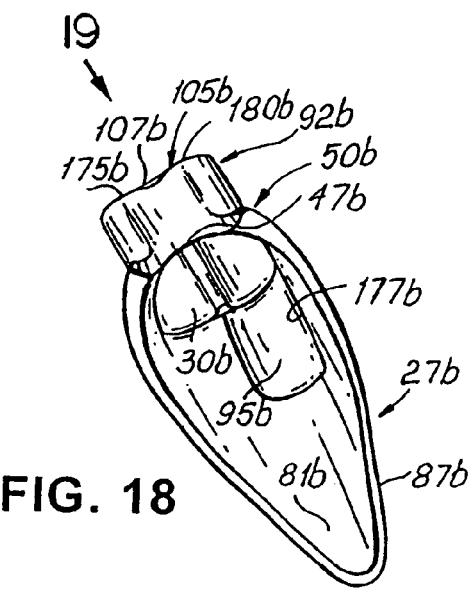
FIG. 18 is an anterior view of a second embodiment of the backplate of FIG. 16.
Figure 17:
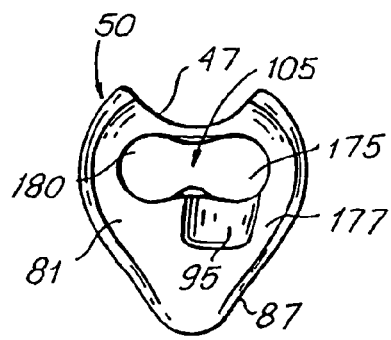
FIG. 17 is a perspective view, in the aspect indicated by line 17 of FIG. 16, showing the recessed heel portion and well, and also showing the double-barrelled passage for the connections of the airway and external-drain tubes.
Figure 19:
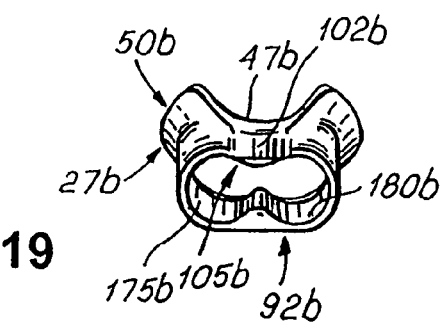
FIG. 19 is a perspective view of the second embodiment of the backplate illustrated in FIG. 18, in the aspect indicated by line 20, showing the recessed heel portion, and the double-barrelled passage for the connections for the airway and external-drain tubes.
Figure 20:
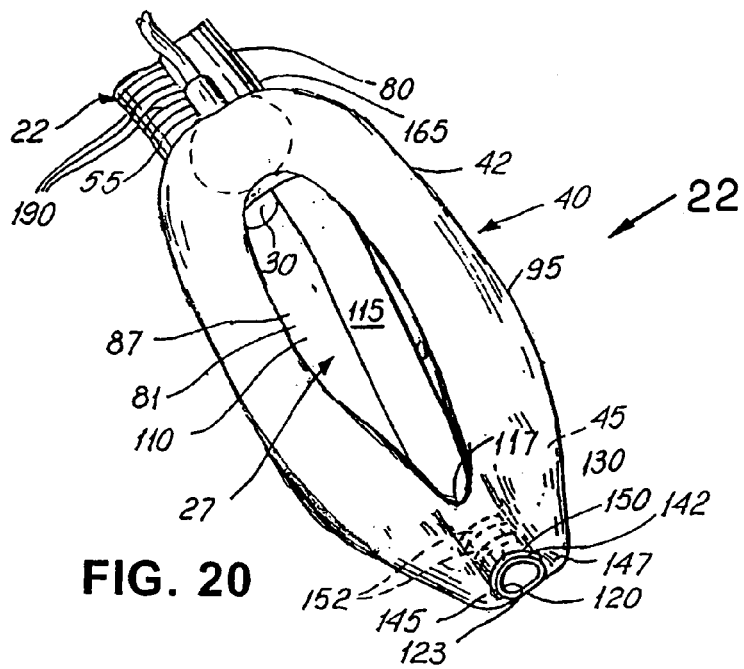
FIG. 20 is a perspective view of the anterior surface of the LMA-device of FIGS. 3 and 7 in a deflated condition.

FIGS. 18 and 19 show a second embodiment of the backplate 27b. Parts in FIGS. 18 and 19 having corresponding parts in FIGS. 16 and 17 have the same reference numeral with the addition of suffix b. The backplate 27b is similar to the backplate 27 illustrated in FIGS. 16 and 17 except that the backplate 27b does not a strap similar to strap 100.

The evacuation tube 80 comprises an internal-drain tube 115 extending between the tube-joint 92 and the distal region 45 of the main-cuff 40 on the laryngeal-side 81 of the backplate 27. The internal-drain tube 115 longitudinally traverses the interior of the distal region 45 of the main-cuff 40 in sealed relation therewith for operative engagement and communication with the inlet of the oesophagus 57. The internal-drain tube 115 is anterior relative to the seam 85 of the main-cuff 40 such that the seam is disposed between the internal-drain tube and the distal end of the oval portion 87.

The internal-drain tube 115 therefore pierces the distal region 45 at the proximal crotch-region 117 and the longitudinally opposing distal crotch-region 120, both of which are portions of the distal region 45. The edges of the main-cuff 40 in the crotch-regions 117, 120 surrounding the internal-drain tube 115 are hermetically sealed to the tube such that the enclosure of the main-cuff 40 is defined in part by the external cylindrical surface of the internal-drain tube.

Figure 14:
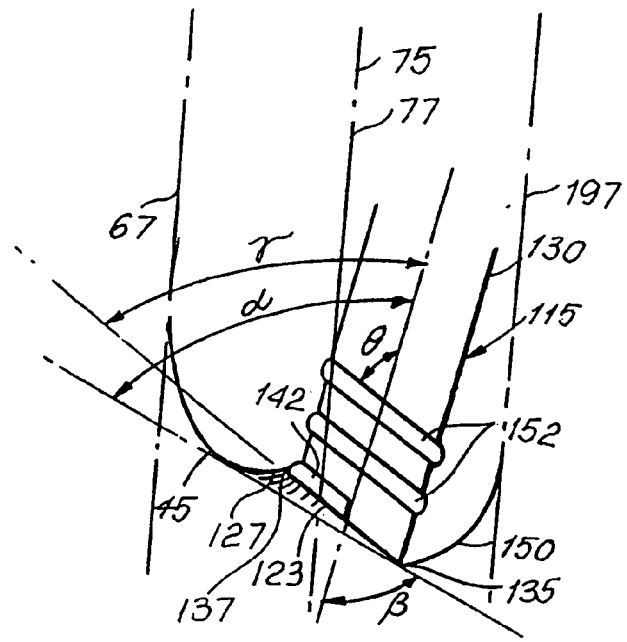
FIG. 14 is an enlarged fragmentary view of a detail of FIG. 8 showing the connection between the external-drain tube and distal region of the main-cuff, the angles between selected parts and respective reference planes also being shown.

The internal-drain tube 115 terminates in an oblique distal orifice 123 opening out on the anterior distal aspect of the distal region 45 of the main-cuff 40. The oblique distal orifice 123 results in partial flattening of the distal region 45 such that the flattening is in a transverse plane inclined relative to the major plane 75 by an angle a of preferably approximately 45 to 50 degrees when main-cuff 40 is inflated, as shown in FIG. 14. When the main-cuff 40 is deflated, angle a is preferably approximately 40 to 45 degrees. In adult sizes of the LMA-device 20, the surface area of the distal region 45 removed to accommodate the orifice 123 is approximately 1 square centimeter which is therefore no longer available to contribute to expansion of the main-cuff 40 when the main-cuff is inflated for sealing around the laryngeal inlet 67. Accordingly, to prevent inspired gas leakage across the distal region 45 resulting from insufficient local expansion of the main-cuff 40, additional circumferential area of the anterior surface of the distal region may be required for sealing. This may be provided by inversion of the anterior-facing lip 127 of the distal region 45 surrounding the orifice 123 resulting from longitudinal withdrawal of the intra-cuff portion 130 of internal-drain tube 115 approximately 3.5 millimeters relative to the plane containing the distal end of the distal region 45 of the main-cuff 40. This inversion produces a corresponding lateral bulging of the distal region 45 around the orifice 123. The anterior position of the distal orifice 123 ensures less compressive force resulting from the fluid pressure inside the main-cuff 40 on the intra-cuff portion 130 in the anterior-posterior direction, thus compensating for anterior-posterior compression from anatomical structures in the throat 32 so that the internal-drain tube 115 is subject to approximately equal compressive forces laterally and anterior-posteriorly, hence avoiding collapse.

The part of the intra-cuff portion 130 containing the distal orifice 123 has a longitudinal central axis inclined relative to the plane containing the distal orifice by an angle .gamma. of preferably 60 degrees, and inclined relative to the major plane 75 by an angle Δ of preferably 20 degrees. The longitudinal central axis of the intra-cuff portion 130 is contained in the sagittal plane 97.

The distal orifice 123 has diametrically opposed posterior and anterior apexes 135, 137. The distal orifice 123 is contained in a transverse elliptical plane preferably inclined by an angle β, which is preferably 40 degrees, relative to the major plane 75, as shown in FIG. 14. The inclination of the distal orifice 123 is such that the posterior apex 135 is offset distally relative to the anterior apex 137 along the longitudinal axis of the portion of the internal-drain tube 115 containing the distal orifice 123.

Figure 9:
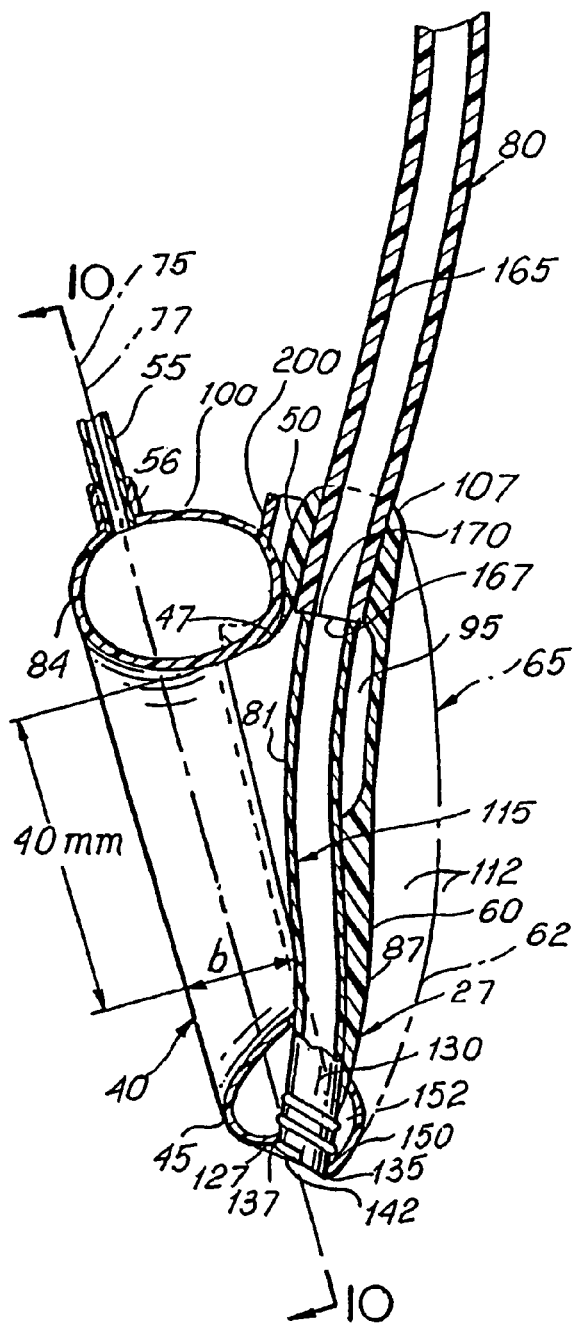
FIG. 9 is a view corresponding to FIG. 8 with portions broken away to show the anterior-posterior dimension of the internal-drain tube relative to a plane containing the anterior surface of the main-cuff.

Integral with the external anterior surface of the intra-cuff portion 130 adjacent to the distal orifice 123 is a semicircular transverse shoulder 142, as shown in FIG. 9. The anterior and the adjacent lateral portions of the distal edge of the distal region 45 of the main-cuff 40 are bonded to the proximal surface of the shoulder 142. The posterior and remaining lateral portions of the distal edge of the distal region 45 are bonded to the unshouldered external surface adjacent to the distal orifice 123.

The lateral termination of each end of the shoulder 142 facilitates collapse of the distal orifice 123 in the major plane 75 when the main-cuff 40 is deflated since the un-reinforced posterior portion of the intra-cuff portion 130 is able to collapse more readily when the pressure inside the main-cuff 40 is reduced (i.e., negative pressure is applied to the main-cuff). Also, by limiting the circumferential dimension of the shoulder 142, its peripheral length which must be deflected is reduced. In contrast, if the shoulder 142 extended posteriorly a sufficient amount such that it traversed the major plane 75, the portions of the shoulder that traversed the major plane would require closure to close distal orifice upon deflation of the main-cuff 40. Such closure of such a shoulder would require significantly more force than required to flatten the shoulder 142, shown in FIG. 14. Such increased force may require stronger material for the main-cuff 40 and application of higher deflation vacuums to the main-cuff.

The distal orifice 123 is withdrawn proximally relative to the distal region 45 of the main-cuff 40 resulting in the portion of the distal region 45 adjacent to the distal orifice 123 being invaginated when the main-cuff 40 is inflated, as shown in FIG. 14. The bonding of the distal end of the distal region 45 to the distal surface of the shoulder 142 results in the transversely-arcuate inverted anterior-facing lip 127 of the invaginated surface having the greatest radial bulge. The transversely-arcuate lateral portions 145, 147 of the invaginated surface have the next largest radial bulge with the transversely-arcuate posterior portion 150 having the least radial bulge. The opposed lateral portions 145, 147 are symmetrical about the sagittal plane 97 of the main-cuff 40.

The portion of the internal-drain tube 115 longitudinally traversing the interior of the distal region 45 of the main-cuff 40 defines intra-cuff portion 130. The outer surface of the intra-cuff portion 130 has at least one circumferential strengthening rib 152 proximal of the shoulder 142 to resist radial collapse of the intra-cuff portion 130 by internally directed radial forces resulting from the fluid pressure within the main-cuff 40. The rib 152 is contained in a transverse elliptical plane preferably inclined at an angle θ, preferably of 60 degrees and equal to angle γ, relative to the longitudinal axis of the intra-cuff portion 130, as shown in FIG. 14. The inclination of the rib 152 enables its posterior pivoting about its posterior apex during deflation of the distal region 45 to facilitate flattening of the main-cuff 40.

The portion of the internal-drain tube 115 proximal of the intra-cuff portion 130 is laterally offset from the sagittal plane 97, as shown in FIGS. 3 and 7. The portion of the internal-drain tube 115 where it emerges from the proximal crotch-region 117 and extends to the well 95 is received in a groove 157 formed in the oval portion 87, as shown in FIG. 7. The groove 157 is defined laterally by fillets 160 which laterally abut the internal-drain tube 115. As much as 50% of the posterior portion of the cross-sectional area of the internal-drain tube 115 may be contained in the distal portion of the groove 157, except where its circumference is free posteriority, i.e., where it runs over the well 95. In one size of the main-cuff 40, the longitudinal dimension of the groove 157 is 2.5 centimeters. The internal-drain tube 115 is welded to the groove 157.

The fillets 160 resist anterior deflection of the oval portion 87 since the fillets provide increased surface area for the weld between the internal-drain tube 115 and oval portion. This additional resistance compensates for the reduced resistance resulting from a reduction in the anterior-posterior thickness of the part of the oval portion 87 defining the base of the groove 157. Such reduced anterior-posterior thickness is desirable to increase the anterior-posterior dimension a between the anterior surface of the main-cuff 40, and the portion of the internal-drain tube 115 between the proximal crotch region 117 and well 95, shown in FIG. 8, especially at the location of dimension b, shown in FIGS. 9 and 10, which should have a depth of at least 10 millimeters in adult sizes, described further herein below.

FIG. 12 illustrates a second embodiment of the LMA-device 20a in which the flexible panel 62a is tethered to the backplate 27a. The parts in FIG. 12 having corresponding parts in FIGS. 1 to 11 have the same reference numeral with the addition of suffix a. Tethering of the panel 62a to the backplate 27a provides additional resistance to anterior inversion of the oval portion 87a. This enables further reduction in the anterior-posterior thickness of the part of the oval portion 87a defining the base of the groove 157a. As discussed above, such reduced anterior-posterior thickness is desirable to increase the anterior-posterior dimension, corresponding to the dimension a in FIG. 8.

A longitudinal portion of the internal-drain tube 115 extends over well 95, as shown in FIG. 8. The anterior-inclination of the portions of the laryngeal-side 81 proximal and distal of the well 95, described herein above, anteriorly props the portion of the internal-drain tube 115 extending over the well to increase the anterior-posterior clearance between the internal-drain tube and base of the well. The internal-drain tube 115 arches over the well 95 defining a slight posterior curve and simultaneously curving laterally to its insertion in the tube-joint 92.

The evacuation tube 80 includes an external-drain tube 165 having a distal end 167 connected in end-to-end relation to the proximal end 170 of the internal drain-tube 115. The joint between the internal and external-drain tubes 115, 165 is located where the tube-joint 92 opens into laryngeal-chamber region 110, as shown in FIGS. 8 and 15.

The inner diameters of the internal-drain tube 115 and external-drain tube 165 are the same. The outer diameter of the internal-drain tube 115 is less than the outer diameter of the external-drain tube 165. The distal end 167 of the external-drain tube 165 has an internal countersunk portion 172 defined by a bevelled internal axial wall, as shown in FIG. 15. The outer diameter of the countersunk portion 172 is greater than the outer diameter of the internal-drain tube 115. The proximal end 170 of the internal-drain tube 115 abuts the countersunk portion 172 resulting in coaxial self-alignment of the central longitudinal axes of the distal and proximal ends 167, 170.

Figure 15:
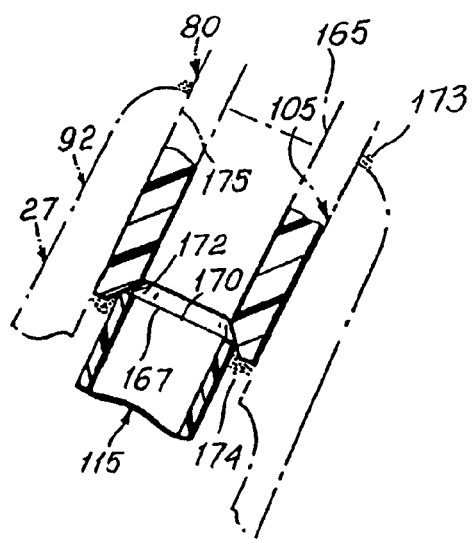
FIG. 15 is an enlarged fragmentary view of a detail of FIG. 8 showing the connection between the internal and external-drain tubes.

As shown in FIGS. 8 and 15, the external-drain tube 165 is supported in the cylindrical drain barrel 175 of the double-barrelled passageway 105 which is longitudinally offset from the well 95 at an angle of approximately 9 degrees. The internal-drain tube 115 is thereby disposed anteriorly of the well 95 and is also offset at 9 degrees from the major axis of drain barrel 175 to increase the lateral clearance.

The evacuation tube 80 is preferably moulded to the backplate 27. Alternatively, for making a prototype, assembly of the evacuation tube 80 to the backplate 27 may be by first welding the distal portion of the internal-drain tube 115 into the distal region 45 of the main-cuff 40. Before connecting the proximal end of the internal-drain tube 115 to tube-joint 92, the main-cuff 40 is welded to the backplate 27. The external-drain tube 165 is then welded into the drain barrel 162 of the tube-joint 92, for example, by an adhesive 173. Hardening of these welds effectively clamps and fixes the distance between the distal end of the proximal crotch-region 117 of the main-cuff 40 and the distal end 167 of the external-drain tube 165. The internal-drain tube 115 is cut, as needed, such that it is slightly longer than this distance. The proximal end 170 of the internal-drain tube 115 is then inserted into the countersunk portion 172 of the external-drain tube 165 with the countersunk portion resulting in coaxial self-alignment of the longitudinal central axes of the distal and proximal ends 167, 170. The internal-drain tube 115 is then welded to the tube-joint 92, for example, by an adhesive 174.

The slightly longer length of the internal-drain tube 115 relative to the distance between the proximal crotch-region 117 and distal end 167 results in a slight longitudinal compression of the internal-drain tube causing lateral curvature of it away from the adjacent side-wall 177 of the backplate 27. Lateral curvature of the internal-drain tube 115 away from the adjacent side-wall 177 increases the lateral clearance between them, reducing the likelihood of dirt collecting between them.

As shown in FIGS. 3 and 7, the airway tube 22 is supported in the cylindrical airway barrel 180 of the double-barrelled passageway 105 in communication with the airway port 30 defined by the opening of the airway barrel 180 into the laryngeal-side 81. Such communication provides a flow-path between the airway tube 22 and laryngeal-chamber region 110. The airway tube 22 is connected to the tube-joint 92 by welding using an adhesive or, alternatively, connected by high-pressure or temperature fusion.

The airway tube 22 and external-drain tube 165 are welded together in side-by-side tangential relation, as shown in FIG. 2. The welding is accomplished by depositing adhesive in one or both of the crevices defined by the outer surfaces of the tubes 22, 165 adjoining the line of tangential contact between them. The adhesive preferably extends longitudinally from the tube-joint 92 proximally for approximately 4¼ inches. Alternatively, the tubes 22, 165 may be connected together by high pressure or temperature fusion. Also, the tubes 22, 165 may be manufactured by simultaneous extrusion. Additionally, the tubes 22, 165 may remain separate for certain clinical applications, e.g., operations on the tongue 202 in the mid-line or other mid-line structures in the pharynx 197.

The airway tube 22 and external-drain tube 165 are inserted through a bite-plate 176 comprising a sleeve which is telescopically fitted around the tubes 165, 176, as shown in FIG. 2. The bite-plate 176 is positioned longitudinally on the tubes 22, 165 such that, when the LMA-device 20 is completely inserted into the throat 32 and pharynx 197, the bite-plate is positioned between the upper and lower teeth, described further herein below.

In embodiments in which the airway tube 22 is bonded to the external-drain tube 165, the tubes 22, 165 are bent away from one another, laterally at the proximal extent of the adhesive to facilitate routing of the airway tube to a ventilating apparatus (not shown) and the external-drain tube 165 to a suction-apparatus (not shown), if required. The separation of the airway tube 22 and external-drain tube 165 is achieved by placing a sleeve 182 on the airway tube to cover the proximal 3 centimeters of the airway tube. The sleeve 182 is proximally oriented relative to the bite-plate 176. Connected to the distal end of the sleeve 182 is a triangular wedge 185 oriented toward the external-drain tube 165 to force the softer external-drain tube to incline away from the airway tube 22 by an angle C, preferably approximately 15 degrees. The sleeve 182 and wedge 185 are a single moulding and are welded to the airway tube 22. Additionally, the wedge 185 is welded to the external-drain tube 165. The sleeve 182 also stiffens the proximal end of the airway tube 22 to reduce the likelihood of kinking at its attachment to the ventilating apparatus (not shown).

The portions of the airway tube 22 and external-drain tube 165 in side-by-side tangential relation each have the same outer diameter. The inner diameter of this portion of the airway tube 22 is greater than the inner diameter of the adjoining portion of the external-drain tube 165. These portions of the airway tube 22 and external-drain tube 165 each have approximately the same stiffness and resistance to longitudinal bending. A metallic cylindrically helical wire 190 is provided between inner and outer surfaces of the airway tube 22 in coaxial relation therewith to increase the kink resistance of the thinner-wall airway tube. The kink resistance of this portion of the airway tube 22 may be further increased by forming it of a material having a harder durometer of silicone. It may also be possible for the chemical compositions of these portions of the tubes 22, 165 to be approximately the same if, for example, the helical wire 190 sufficiently increases the stiffness of airway tube.

A hard plastic or polycarbonate cylindrical fitting (not shown) is inserted in the end of the airway tube 22 proximal of the triangular wedge 185. The fitting is inserted into the airway tube 22, and has a radial flange which abuts the proximal end of the airway tube to longitudinally limit the insertion of the fitting into the airway tube. The fitting facilitates connection to the ventilating apparatus (not shown).

In use, an inflation/deflation device is actuated to apply a vacuum, via the tube 55, to the main-cuff 40 sufficient to fully deflate it prior to insertion of the main-cuff through the mouth of the patient. Such a vacuum extends to the space enclosed by the flexible panel 62 and backplate 27, via the channel 90 in the main-cuff 40, deflating the back-cuff 65 to collapse it onto the pharyngeal-side 60 of the backplate 27 and posterior surface of the main-cuff.

The main-cuff 40 is preferably deflated into a predetermined shape by using the forming tool disclosed in U.S. Pat. No. 5,711,293, the entire disclosure of which is hereby incorporated by reference herein.

The flattened sheet, comprising fully deflated the main-cuff 40, backplate 27 and internal-drain tube 115, is passed easily through the mouth 25 of the patient because of the reduced compressible antero-posterior dimension of the part of the LMA-device 20 having the largest anterior-posterior dimension, i.e., the generally proximal region 42 of the main-cuff 40 and the heel 50. This reduced compressible antero-posterior dimension results from the recess 47 of the heel 50. The deflated main-cuff 40, backplate 27 and internal-drain tube 115 is pressed against the hard and soft palates 192, 195 as it is pushed inwardly, resulting in the deflated main-cuff being guided distally by the soft palate onto the posterior wall of the pharynx 197. Such deflection of the main-cuff 40 is normally only reliably achieved if the total stiffness of the LMA-device 20 is within certain predetermined limits.

The main-cuff 40 is preferably urged through the throat 32 by placement of either the operator's index finger or an insertion tool inserted into the strap 200 against the heel 50, because the side-by-side airway tube 22 and internal-drain tube 115 are normally not sufficiently stiff to be used as a rod to direct the main-cuff through the throat.

The main-cuff 40 is preferably positioned in the throat 32 by inserting the a sufficient length of the index finger of the operator through the introducer tool slot 201 such that the finger is placed on the mid-line groove 102 of the tube-joint 92 and the end of the finger abuts the heel 50, as shown in FIG. 16. Inserting the finger through the introducer tool slot 201 enables the finger to be partly wedged into the strap 100 to secure the index finger to the mid-line groove 102. Placement of the index finger on the mid-line groove 102 of the tube-joint 92 and against the heel 50 assists in locating and stabilizing the finger against the proximal region 42 of the main-cuff 40. This reduces the risk of finger slippage from its intended position on the backplate 27 due to the presence of slippery secretions in the mouth 25 and/or the application of lubricant, to assist smooth passage of the LMA-device 20 during its insertion into the patient and to avoid the risk of injury to the patient or of damage to the LMA-device. During such insertion, the proximal region 42 of the main-cuff 40 provides a fulcrum.

An alternative and equally preferable way to position the main-cuff 40 in the throat 32 is by an introducer tool (not shown) including a relatively rigid elongate member having a distal end adapted for removable keyed engagement with the heel 50 and strap 200 adjacent to the tube-joint 92 for insertional guidance of the main-cuff 40. During such insertion, as with placement of the operator's finger against the heel 50, the proximal region 42 of the main-cuff 40 provides a fulcrum. The introducer tool and LMA-device 20 may both be included in a kit.

Preferably, the deflated main-cuff 40 and backplate 27 are sufficiently flexible that they do not overcome the resistance provided by the soft palate 195. The main-cuff 40 and backplate 27 are preferably flexible similar to a palette knife such that, when the main-cuff and backplate are urged or tensed against the soft palate 195, the distal region 45 is deflected downward by the soft palate rather than being forcibly driven into it, which may bruise the soft palate. Also preferable is for the deflated main-cuff 40 to itself bend smoothly around (i.e., in the shape of) an arc 196, as shown in FIG. 21, also similar to a palette knife.

Further, the deflated main-cuff 40 and backplate 27 resist kinking. Kinking results in the main-cuff 40 and backplate 27, during their insertion through the throat 32, collapsing on the tongue 202 rather than arching over it. To avoid kinking, a specific overall stiffness and long-axis gradation of stiffness in the delated main-cuff 40 is required, which in turn depends on the shape of the backplate 27. The primary factors or considerations to be balanced when designing the backplate 27 are (i) desirability of long-axis gradation of stiffness (i.e., linear tapering-off distally of resistance to flexure), (ii) adequate stiffness and appropriate architecture to prevent anterior herniation from fluid pressure within the inflated back-cuff 65, and (iii) minimal thickness in the anterior-posterior dimension to reduce overall resistance to flexure.

The relative stiffness of the airway tube 22, external-drain tube 165 and backplate 27 facilitate piloting and guiding of the substantially flattened, deflated main-cuff 40 to smoothly ride or track posterior contours of the throat 32 and pharynx 197 and to assure that the deflated main-cuff enters and locates immediately above the upper oesophageal sphincter 207 and adjacent to the laryngeal inlet 67, as shown in FIGS. 1 and 2.

Figure 21:
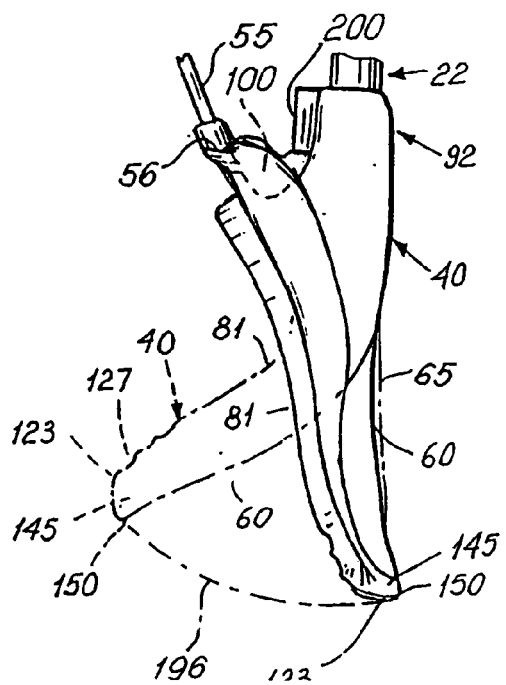
FIG. 21 is a lateral view of the main-cuff in the direction indicated by line 22 of FIG. 20 showing the preferred deflection characteristic of the main-cuff.
Figure 22:
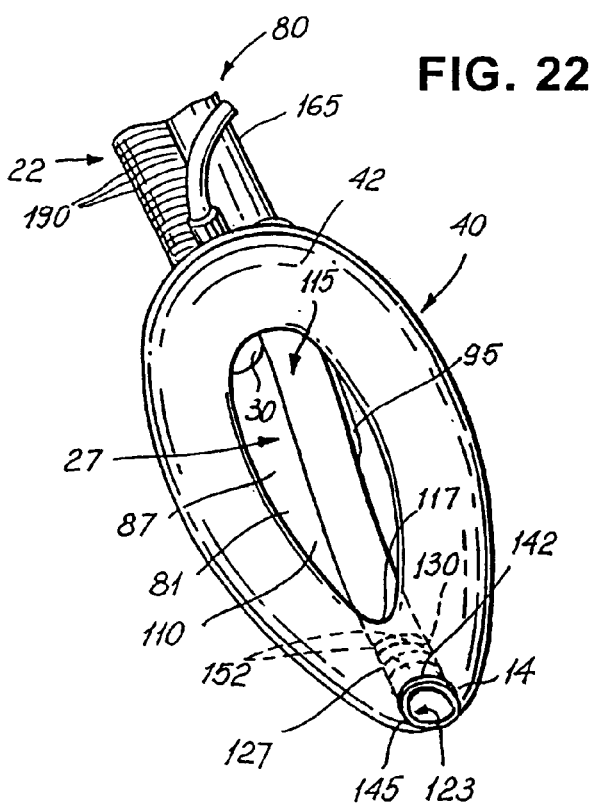
FIG. 22 is a perspective view in the aspect of FIG. 20 showing the LMA-device of FIGS. 3 and 7 in an inflated condition.

Additionally, the backplate 27, internal-drain tube 115 and main-cuff 40 are sufficiently flexible to allow anterior and posterior deflection of the distal region 45 in the sagittal plane 97 when the main-cuff is fully deflated, as shown in FIG. 21. Such deflection further facilitates riding or tracking of the distal region 45 of the main-cuff 40 over the posterior contours of the throat 32 by allowing the distal region to deflect as necessary to conform to protrusions or recesses in the posterior surface of the throat.

The deflated main-cuff 40 further enters into its correct position opposite the laryngeal inlet 67 without colliding with anterior structures such as the posterior surface of the tongue 202, epiglottis 35, or arytenoids 205. Insertion of the deflated main-cuff 40 is facilitated by forming the main-cuff 40 and attaching it to the backplate 27 such that the seam 85 abuts the backplate, as shown in FIGS. 12, 13 and 14. As a result, when the main-cuff 40 is fully deflated, the anterior surface of the main-cuff is uninterrupted by the seam 85, i.e., the seam is buried between the backplate 27 and the deflated main-cuff. Accordingly, the likelihood is reduced of the anterior surface of the deflated main-cuff 40 scraping or catching on the anatomical structures of the throat 32, such as the epiglottis 35 and arytenoids 205. Further disclosure of insertion of the deflated main-cuff 40 through the throat 32 may be had by reference to U.S. Pat. No. 5,632,271, the entire disclosure of which is hereby incorporated by reference herein.

When the LMA-device 20 is fully inserted in the throat 32, the side-by-side airway tube 22 and external-drain tube 165 extend proximally from the tube-joint 92 in contacting relation with the soft palate 195, and lie against the hard palate 192, i.e., the roof of the mouth 25. The tubes 22, 165 are spaced inwardly of the sides of the throat 32 to avoid damage to the lingual nerves. The tubes 22, 165 rest lightly against the posterior aspect of the upper teeth, usually close to parallel with the inner surface of the upper incisors, and emerge from the mouth 25 between the teeth.

The bite-plate 176 is positioned at the emergence of the tubes 22, 165 from the mouth 25 such that the bite-plate is disposed between the upper and lower teeth and the tubes. The teeth thereby directly contact the bite-plate 176, rather than the tubes 22, 165, to provide protection to the tubes.

When the main-cuff 40 is correctly positioned, the distal orifice 123 of the internal-drain tube 115 contacts the upper oesophageal sphincter 207 and lies posterior to the cricoid cartilage 210. The bevelled distal region 45 of the main-cuff 40, including the distal orifice 123 of the internal-drain tube 115, forms a wedge-shape of approximately 45 degrees when the main-cuff 40 is deflated. This facilitates insertion of the main-cuff 40 and backplate 27 behind the cricoid cartilage 210 because such insertion requires the cricoid cartilage to be gently forced anteriorly to allow passage of the wedge-shaped distal region 45, including the distal orifice 123, behind it. Further disclosure of positioning the LMA-device 20 may be had by reference to U.S. Pat. No. 5,241,956, the entire disclosure of which is hereby incorporated by reference.

When the LMA-device 20 is completely inserted, the main-cuff 40 contacts the base of the hypo-pharynx 212 with the distal region 45 being wedged into the upper opening of the upper oesophageal sphincter 207, a constriction which is however much too small to permit the LMA-device 20 to pass through it. Complete insertion of the LMA-device 20 is thereby detected by the operator as a resistance to insertion of the main-cuff 40 into the upper oesophageal sphincter 207. The main-cuff 40 is then inflated with sufficient air, via the tube 55, to obtain a seal against the laryngo-pharyngeal perimeter. The LMA-device 20, when completely inserted in the pharynx 197, lies in the sagittal plane 97.

Inflation of the main-cuff 40 causes expansion of the distal region 45 enabling it to lie against and adapt to the pharynx 197 and hypo-pharynx 212. Additionally, inflation of the main-cuff 40 causes the gas or fluid to flow into the space enclosed by the flexible panel 62 and backplate 27, for example, via one or more ports in the main-cuff, resulting in inflation of the back-cuff 65. Inflation of the back-cuff 65 initially causes engagement between the flexible panel 62 and posterior surface of the pharynx 197. Further inflation of the back-cuff 65 urges the main-cuff 40 anteriorly to press it against the tissue surrounding the laryngeal inlet 67. This tightens the sealing engagement between the main-cuff 40 and the tissue surrounding the laryngeal inlet 67, thereby reducing leakage between such tissue and the main-cuff. The sealing engagement is further improved by provision of the increased anterior-posterior space between the oval portion 87 of the backplate 27 and the anterior surface of the main-cuff 40, permitting accommodation of the posteriorly bulging posterior surface of the cricoid cartilage 210 which is located distally relative to the laryngeal inlet 67.

If the back-cuff 65 is overinflated, the oval portion 87 may bulge anteriorly outward resulting in anterior displacement of the internal-drain tube 115 relative to the main-cuff 40, and loss of the advantageously increased anterior-posterior space between the oval portion 87 and the anterior surface of the main-cuff 40, described above. The anterior-posterior dimension a between the anterior tangency of the internal-drain tube 115 and a plane containing the anterior surface of the main-cuff 40, shown in FIG. 8, must not decrease below a minimum level since such may result in the internal-drain tube undesirably impinging against anatomical structures of the throat 32 normally present in the laryngeal-chamber region 110. For example, if the main-cuff 40 is a standard adult size and is inflated to 40 millimeters Hg (mercury), at a point b contained in the sagittal plane 97 and located 40 millimeters distally from the distal end of the proximal region 42 of the main-cuff 40, shown in FIG. 9, the minimum anterior-posterior distance b must not approach 8 millimeters, is preferably at least 10 millimeters and ideally at least 10.7 millimeters.

The transversely arched profile, degree of hardness, and increased anterior-posterior thickness of the distal portion of the oval portion 87 are all factors chosen to offer adequate resistance to such anterior bulging thereby limiting such resulting anterior displacement of the internal-drain tube 115 near the distal region 45 of the main-cuff 40 where the internal-drain tube is nearest to the anterior surface of the main-cuff. Fillets 160, 160a and tethered panel 62a, shown in FIGS. 11 and 12, also limit anterior displacement of the internal-drain tube 115 relative to the main-cuff 40. Anterior-posterior dimension a, shown in FIG. 8, should be maintained above a minimum amount to avoid anterior displacement of the arytenoids 205 which may obstruct flow of gases through the larynx 37, and to avoid anterior displacement of anatomical structures relative to the main-cuff 40 which may reduce the tightness of the seal between the main-cuff and the tissues surrounding the laryngeal inlet 67. Additionally, the backplate 27 is preferably sufficiently flexible to deflect in the anterior-posterior direction during insertion into the throat 32 to follow its contours, e.g., to bend around the soft palate 195.

The backplate 27 is reinforced because the prior LMA-devices (such as is disclosed in U.S. Pat. No. 4,509,514) did not have a back-cuff, such as back-cuff 65. The back cuff 65 of the LMA-device 20 causes pressure to be applied to the oval portion 87 of the backplate 27, which may cause the oval portion to herniate anteriorly. The backplate 27 must therefore be designed to resist such herniation, preferably to pressures within back-cuff 65 of up to 100 centimeters of water. Techniques for preventing such herniation of the backplate 27 include arching the backplate 27 such that it has a concavity facing anteriorly, making the backplate of a high durometer silicone or other plastics material, thickening the backplate sufficiently to resist herniation (but not so much that it becomes too stiff to bend easily around the back of the tongue 202), and possibly also providing the backplate with a midline longitudinally running 30 groove for accurately locating adhesive to weld to it the back cuff 65. In addition, the back cuff 65 may be made of a thin elastomeric sheet material capable of considerable elongation in response to the pressure within it, resulting in minimal herniation of the backplate 27.

The anteriorly facing laryngeal-chamber region 110 of the main-cuff 40 is wider than the transverse distance between the edges of the laryngeal inlet 67 as defined by the so-called aryepiglottic folds which bilaterally border the laryngeal inlet thus encouraging a sealing contact between the main-cuff and the pharyngeal tissues as well as the tissues bordering the laryngeal inlet. The main-cuff 40 is thus functionally a pharyngo-laryngeal mask airway forming an end-to-end seal against the larynx 37.

FIGS. 23 and 24 illustrate a third embodiment of the LMA-device 20c. Parts in FIGS. 23 and 24 having corresponding parts in FIGS. 1 to 22 have the same reference numeral with the addition of suffix c. The main-cuff 40c may have soft and yielding ridges (not shown) bilaterally disposed on the anteriorly-facing distal region 45c of the main-cuff which are suitably contoured to fill the anatomical grooves known as the pyriform fossae to increase the sealing efficacy of the main-cuff. The LMA-device 20c exploits the triangular cross-section of the grooves of the pyriform fossae which are roofed over and isolated by the anterior surface of the main-cuff 40c bilaterally. The entire length of the grooves of the pyriform fossae are covered by the main-cuff 40c such that a respective cavity is defined by each groove and the contiguous portion of the anterior surface of the main-cuff. Incorporation of one or more one-way valves 215, such as a reed or duck-bill valve, in the anterior wall of the main-cuff 40c facing the grooves of the pyriform fossae permits the operator to evacuate residual gas from the cavities by anterior neck pressure so causing the low pressure in the cavities to pull or draw the main-cuff anteriorly enhancing the seal. One-way valves 215 may be duck-bill valves of the type sold by Accusil® Incorporated of Merriville, Ind., U.S.A.

Attached to the interior surface of the anterior wall of the main-cuff 40c are respective cylindrical housings 217, shown in FIG. 24, each surrounding a respective one of the one-way valves 215. Deflation of the main-cuff 40c draws its posterior wall toward the housings 217 and one-way valves 215, eventually causing the posterior wall to seat on the open posterior ends of the housings 217, as illustrated by a portion of the posterior wall being shown in phantom line in FIG. 24 in dashed lines. Seating of the posterior wall of the main-cuff 40 on the open posterior ends of the housings 217 hermetically seals the respective one-way valves 215 from the remainder of the interior of the main-cuff. Each of the one-way valves 215 thereby becomes isolated from the reduced pressure inside the main-cuff 40c. This prevents the reduced pressure within the main-cuff 40c from drawing gases external of the main-cuff in the vicinity of the one-way valves 215 through the one-way valves into the main-cuff thereby enabling the reduced pressure inside the main-cuff to deflate it.

In an alternative embodiment (not shown), one-way valves 215 and their associated housings 217 may be replaced by ports or apertures, the ends of which within the main-cuff 40c are each connected to a tube also within the main-cuff. The tubes connected to the ports or apertures communicate via a tube or, less preferably, multiple tubes which extend through the wall of the main-cuff to a point outside of the main-cuff 40c such that the ports or apertures, and the tubes connected to them, are isolated from the interior of the main-cuff. A source of suction may then applied to the tube or tubes outside of the main-cuff 40c to evacuate residual gas from the cavities defined by each groove of the pyriform fossae and the contiguous portion of the anterior surface of the main-cuff.

The sealing efficacy of the main-cuff 40 may be further increased by an optional wedge-shaped crescent (not shown) in sealing contact with the anterior surface of substantially the proximal one-half of the main-cuff.

The epiglottis 35, a leaf-like structure which normally projects proximally and posteriorly, is supported against the anterior surface of the internal-drain tube 115. The internal-drain tube 115 thereby defines a stop to prevent the epiglottis 35 from interfering with communication between the airway tube 22, via the airway port 30, and the laryngeal inlet 67. This creates adequate space in the laryngeal-chamber region 110 posterior to the epiglottis 35 for passage of gases between the airway port 30 and laryngeal inlet 67.

Such passage of gases between the airway port 30 and laryngeal inlet 67 is mainly in the portion of the laryngeal-chamber region 110 lateral of the sagittal plane 97 and containing the airway port. If, however, the epiglottis 35 slides laterally from its propped position against the internal-drain tube 115 into the lateral portion of the laryngeal-chamber region 110 containing the airway port 30, gas passage between the airway port and laryngeal inlet in this portion of the laryngeal-chamber region may be obstructed. If so, gases may circulate between the airway port 30 and laryngeal inlet 67 via the radial clearance between the internal-drain tube 115 and well 95, and through the portion of the laryngeal-chamber region 110 laterally of the sagittal plane 97 offset from the airway port 30. An alternative circulation flowpath is thereby provided to permit adequate and free gas communication between the airway tube 22 and laryngeal inlet 67, while simultaneously preventing obstruction to such gas flow by the epiglottis 35. The contour of the laryngeal-side 81 of the backplate 27 props the internal-drain tube 115 away from the laryngeal-side to facilitate sufficient radial clearance between the internal-drain tube 115 and well 95 thereby to provide the adequate and free gas communication between the airway tube 22 and laryngeal inlet 67.

The oval portion 87 of the backplate 27 has a sufficiently large anterior-posterior depth to contain the internal-drain tube 115 such that the drain tube does not bear against other laryngeal structures and interfere with gas flow.

The well 95 also provides a route for drainage of secretions from the trachea, which may enter the laryngeal-chamber region 110 via the laryngeal inlet 67. Such secretions normally collect in the well 95 since, when the LMA-device 20 is fully installed and the patient is supine, the laryngeal-side 81 of the backplate 27 faces upward. In the absence of the well 95, such secretions would collect between the laryngeal-side 81 of the backplate 27 and internal-drain tube 115.

The adequately-sized well 95 is provided behind the internal-drain tube 115 to allow gases or secretions to pass between the internal drain tube and the backplate 27. This improves drainage of secretions emerging from the trachea 36 and improves gas exchange if there is any obstruction due to the epiglottis 35 falling into the laryngeal-chamber region 110 close to the distal-end 72 of the airway tube 22 adjacent to the airway port 30.

Inflation of the main-cuff 40 causes expansion of the distal region 45 including the anterior-facing lip 127, lateral portions 145, 147, and posterior portion 150 of the invaginated end, as shown in FIGS. 8 and 14. The hermetic seal between the oblique distal orifice 123 of the internal-drain tube 115 and the distal region 45 of the main-cuff 40 obstructs communication between the oesophagus 57 and laryngeal-chamber region 110. Accordingly, leakage, e.g., of contents from the oesophagus 57 into the laryngeal-chamber region 110, and via the laryngeal inlet 67 into the trachea is obstructed.

The invagination and 45 degree angulation of the distal end of the main-cuff 40 reduces the likelihood of leakage between the distal orifice 123 of the internal-drain tube 115 and the laryngeal-chamber region 110 of the main-cuff 40 which may result from the expansion of the main-cuff being hampered at the narrower distal region 45 and distal end by the presence of the distal orifice. Also, the angle formed by the main-cuff 40 when deflated was sufficiently large to impede insertion of the LMA-device 20 to its correct location in the pharynx 197 opposite the laryngeal inlet 67. The desired insertion characteristics are obtained by invagination by 3.5 millimeters (size 4) of the wall of the main-cuff 40 forming the anterior lip 127 of the distal orifice 123 produced an increased expandable area around the distal orifice of the internal-drain tube 115, improving the seal and, by drawing proximally only the anterior lip 127, sufficiently sharpening the angle of the distal tip of the deflated main-cuff.

The side-by-side bonded adjacency of the airway tube 22 and external-drain tube 165 conforms to the cross-sectional shape of the mouth 25 and throat 32 facilitating insertion into and displacement through the throat. The side-by-side adjacency of the airway tube 22 and external-drain tube 165 also reduces the likelihood of kinking when they bend.

After positioning the main-cuff 40 opposite the laryngeal inlet 67 as described herein above, the ventilating apparatus (not shown) is actuated, as needed, to provide anesthesia gas to the trachea, via the laryngeal inlet, through the airway tube 22.

The evacuation tube 80 has the following functions:

(i) the evacuation tube 80 allows gases to be administered to the lungs through the airway tube 22 under positive pressure without the risk of inflating the stomach, via the upper oesophageal sphincter 207, since gases escaping from the laryngeal-chamber region 110 between the main-cuff 40 and the tissues surrounding the laryngeal inlet 67 into the hypo-pharynx 212 will be ducted out through the evacuation tube instead of being forced through the upper oesophageal sphincter 207 into the oesophagus 57, the latter of which may occur with other known LMA-devices such as is disclosed in U.S. Pat. No. 4,509,514 which is hereby incorporated by reference herein;

(ii) conversely, if there is no evidence of gases being ducted through the evacuation tube 80 during positive pressure ventilation through the airway tube 22, this indicates proper positioning of the main-cuff 40 with its distal end of the distal region 45 pressed into the base of the hypo-pharynx 212. The evacuation tube 80 thus provides monitoring of correct placement of the LMA-device 20;

(iii) In the event of unexpected regurgitation though the upper oesophageal sphincter 207, gastric contents are likely to follow the path of least resistance and enter into the evacuation tube 80 through the oblique orifice 123 rather than the larynx 37 via the laryngeal inlet 67, the latter of which may occur with other known LMA-devices such as is disclosed in U.S. Pat. No. 4,509,514 which is hereby incorporated by reference herein; and (iv) If desired, a suction catheter (not shown), probe for monitoring temperature or other parameter (not shown), or endoscope (not shown) may be inserted through the evacuation tube 80 provided the outer diameter of any such inserted device is less than the internal diameter of the evacuation tube.

An additional drain tube (not shown) may also be inserted though the airway tube 22 in a distal direction to emerge through the airway port 30 adjacent to the well 95. A suction may be applied to such additional drain tube to remove secretions which may collect in the well 95. The different inner diameters of the airway tube 22 and external-drain tube 165 facilitate their respective identifications by the operator so to facilitate insertion into the proper tube of such additional drain-tubes or endoscope.

The internal- and external-drain tubes 115, 165 have different external but the same internal diameters because the external-drain tube must be soft in order to bend around the tongue 202 without exerting undue pressure on it. For example, a disadvantage of the airway tube of the LMA-device disclosed in U.S. Pat. No. 4,509,514 is that it may be too stiff. If the external-drain tube 165 is too soft, however, it may kink unless it has a sufficient wall-thickness. The airway tube 22 must be of maximum internal diameter for optimal gas flow through it but of minimum outside diameter to reduce its cross-sectional area and consequent bulk. The resulting outer diameter of the airway tube 22, about 11 millimeters (for #4), is therefore applied to the outer diameter of the external-drain tube 165. The tubes 22, 165 therefore have the same or similar outer diameter, but for different reasons.

The portion of the internal-drain tube 115 contained in the laryngeal-chamber region 110, however, preferably also has a reduced outer diameter to prevent it from interfering with free passage of gases within the laryngeal-chamber region. Additionally, the inner diameter of the internal-drain tube 115 is the same as the inner diameter of the external-drain tube 165 because if the inner diameter of the internal-drain tube is less than the inner diameter of the external-drain tube, the clinician will not know if a catheter inserted through the external-drain tube from outside the mouth will pass through the internal-drain tube. If the inner diameter of the internal-drain tube 115 is less than the inner diameter of the external-drain tube 165, then a catheter just able to pass through the external-drain tube (e.g., the catheter having an outer cross-sectional area which is slightly smaller than that of the external-drain tube) will become obstructed when it reaches the internal-drain tube having the narrower internal cross-section.

Conversely, if the inner diameter of the internal-drain tube 115 is larger than the inner diameter of the external-drain tube 165, then the outer diameter of the internal-drain tube must be correspondingly larger resulting in the internal-drain tube having a larger outer cross-sectional area thereby occupying additional space in the laryngeal-chamber region 110 (free space within the laryngeal-chamber region is precious). The additional internal cross-sectional area of the internal-drain tube 115 resulting from its larger inner diameter would, however, limited use since, for example, the gastric flow volume through the internal-drain tube would be limited by the smaller internal cross-sectional area of the external-drain tube 165.

Anatomical Structures

Ary-epiglottic folds—wings of tissue joining the arytenoid cartilages 205 to each side of the epiglottis 35.

Arytenoid Cartilages 205—a pair of pyramid-shaped cartilages bordering the posterior rim of the laryngeal inlet 67. Arytenoid cartilages 205 are attached anteriorly to the vocal cords which they open, close, lengthen and shorten by rotation and sliding actions, pulled by the laryngeal muscles. The most important of the arytenoid cartilages 205 is the posterior crico-arytenoid muscle, which draws the vocal cords open to permit air to enter and leave the lungs.

Cervical vertebrae—the neck bones, of which there are seven counting from above downwards. The sixth vertebral body lies opposite the cricoid cartilage 210 and the distal tip of the LMA-device 20 lies between the two when correctly inserted.

Constrictor muscles—three cylinders of muscle stacked within each other like plastic cups surround the interior space of the pharynx 197 and act sequentially to squeeze swallowed food into the oesophagus 57. The lower pharyngeal constrictor muscle is the one which mostly wraps around the inserted LMA-device 20. The lowest part of this muscle (most distal part) forms a complete ring and defines the upper oesophageal sphincter 207, also known as the crico-pharyngeus muscle.

Cricoid cartilage 210—a ring of cartilage which acts as the container or chamber of the larynx 37. Cricoid cartilage 210 is attached distally to the trachea or wind-pipe 36. From the lateral sides of the cricoid cartilage 210, the membrane forming the vocal cords stretches upwards and medially. Proximally, the thyroid cartilage surrounds the cricoid cartilage 210 but overlaps it on either side postero-laterally. Posteriorly, the broad flat surface (lamina) of the cricoid cartilage 210 carries the paired posterior crico-arytenoid muscles, which are separated in the mid-line by a ridge. There is normally no space between the muscle-covered lamina an the posterior wall of the pharynx 197, so when the LMA-device 20 enters this area of the pharynx, the LMA-device 20 must squeeze in between these two normally contiguous surfaces. Hence the need to make the deflated LMA-device 20 form a suitable wedge-shape with sufficient resilience to slip in behind (posterior to) the cricoid 210. The part of the internal-drain tube 115 which is enclosed by the distal region 45 of main-cuff 40 of the LMA-device 20 lies immediately posterior to the mid-line ridge on the back of the cricoid cartilage 210. Were the LMA-device 20 to lie to one or other side, it might compress one or other of the vitally important posterior crico-arytenoid muscles.

Cricopharingeus muscle—same as upper esophageal sphincter 207. Part of the inferior constrictor muscle of the pharynx 197.

Epiglottis 35—a fibro-elastic cartilage often described as leaf-shaped, whose pointed end is firmly attached to the posterior surface of the front of the thyroid cartilage and whose lateral borders are suspended between the ary-epiglottic folds, so that its free posterior surface projects proximally and posteriorly. This free posterior surface acts like a shield preventing food entering the glottis but can also cause obstruction to air-flow especially when the pharyngeal space sags inwardly as surrounding muscles weaken during anaesthesia. If the space available inside the LMA-device 20 is inadequate, the epiglottis 35 potentially causes obstruction, particularly if it is large and floppy as may be the case in elderly males. The epiglottis 35 may be downfolded over the laryngeal vestibule if the distal tip of main-cuff 40 catches it and flips it downwards during insertion. Correct deflation and insertion of the LMA-device 20 minimise this risk, as does a good design permitting the optimal wedge-shape of the deflated LMA-device.

Oesophagus 57—muscular tube which is normally closed, unlike the trachea 36 which lies immediately anterior to it. The muscular coat is thickened to form the upper oesophageal sphincter 207 and lower oesophageal sphincter. Stimulating the upper oesophageal sphincter 207 excessively by insertion of a bulky device or inflation of the LMA-device 20 to too high a pressure may cause the upper oesophageal sphincter 207 and lower oesophageal sphincter to open reflexively, making regurgitation of gastric contents more likely. Also, the esophageal muscles tend to relax during anaesthesia, so if there is any obstruction to inspiration, as caused for example by closure of the glottis or a misplaced LMA-device 20, the chest movement of inspiration may cause such a high negative pressure within the chest cavity that the thin-walled oesophagus 57 is literally sucked open, encouraging fluids to be drawn up into it from the stomach. A correctly placed LMA-device 20 with a hole in the distal end, e.g., distal orifice 123, communicating with the oesophagus 57 may prevent this cycle of events from occurring, since it permits air to be drawn into the oesophagus from above.

Glottis—the constriction of the airway tube 22 which occurs in the region of the vocal cords. The larynx 37 is the structure which surrounds and controls the movements and shape of the glottic opening.

Hard Palate 192—the dome shaped bony vault which arches over the upper surface of the tongue 202. The soft palate 195 is attached to it posteriorly and it stretches down to the dental arcades anteriorly and laterally. The anterior surface of the hard palate 192 blends with the gums and is innervated with nerves which trigger deglutition. Hence the importance of stimulating the anterior surface of the hard palate 192 when inserting the LMA-device 20, which must be designed so that when deflated, its posterior surface forms a smooth broad sheet which imparts a soft, atraumatic feel to the surface of the hard palate 192, stimulating the acceptance of the LMA-device 20 by triggering deglutition reflexes rather than rejection of the LMA-device, e.g., triggering vomiting reflexes.

Hyoid bone—a semicircular ring of bone vital to the mechanical 0.5 functions of swallowing, including opening of the mouth 25. The hyoid bone lies above, i.e., proximal to, the thyroid cartilage and is attached above to the base of the tongue 202, the front of the mandible and the base of the skull. The lower part of the hyoid bone is attached to the chest wall, the thyroid cartilage and the pharyngeal constrictor mechanism. The lateral wings of the hyoid bone press into the sides of the inflated main-cuff 40 of the LMA-device 20 near the proximal region 42 of the main-cuff 40. The hypoglossal nerves pass near the inner ends of the hyoid bone, limiting the pressure which should be safely generated within the main-cuff 40 and the lateral expansion permissible in any device inflated in this region of the pharynx 197.

Hypo-pharynx 212—the region of the pharynx 197 lying behind the larynx 37, and normally a closed sack at the level of the cricoid 210. Adjacent to the base of hypo-pharynx 212 is the closed upper oesophageal sphincter 207. The hypo-pharynx 212 is surrounded by the middle and lower constrictor muscles. Anteriorly, the distal region of the hypo-pharynx 212 is bordered by the posterior surface of the cricoid cartilage 210. Also anteriorly, the proximal region of the hypo-pharynx 212 is bordered by the laryngeal vestibule.

Inter-arytenoid muscle—the muscle joining the two arytenoid cartilages 205 posteriorly and transversely, and proximal to the upper border of the cricoid cartilage 210. The inter-arytenoid muscle consists of two parts, a straight transverse part and an "X" shaped part, both of which enable closure of the glottis. The distal end of the bowl which defines the posterior surface of the laryngeal-chamber region 110 of the LMA-device 20 must have adequate depth to avoid interfering with the inter-arytenoid muscle or with the arytenoid cartilages 205 which lie immediately anterior to it. Bruising of the overlying mucosal surface is common with improper insertion of the LMA-device 20.

Larynx 37—the apparatus responsible for protecting the entrance to the lungs from contamination and for vocalisation. The principle advantage of the LMA-device 20 is that it permits the larynx 37 to retain these functions, of which the first is the most important. Endotracheal intubation prevents effective coughing, which is an airways-cleaning mechanism vital to our survival.

Laryngeal inlet 67—the rim of tissue surrounding the vestibule of the larynx 37, consisting of the ary-epiglottic folds laterally, the tip of the epiglottis 35 proximally, and the arytenoids 205 and inter-arytenoid notch distally.

Laryngeal vestibule—a pocket of space above the vocal cords bounded laterally by the quadrate membranes, proximally by the epiglottis 35 and distally by the vocal cords. The distal tip of the LMA-device 20 may lodge in the laryngeal vestibule if the tip does not pass posterior to the arytenoids 205. The laryngeal vestibule closes during swallowing, partly by the action of the ary-epiglottic muscle which acts like a sphincter and partly by the elevation of the larynx 37. This closure of the laryngeal vestibule is observed when the LMA-device 20 is inserted prematurely.

Posterior crico-arytenoid muscle—the most important muscle of the larynx 37 because it acts to separate the vocal cords. The posterior crico-arytenoid muscle lies as a pair of muscles on the posterior surface of the cricoid lamina, which is the broad posterior region of the cricoid cartilage 210. The distal tip of the LMA-device 20 presses against the cartilaginous ridge which separates the two muscles. Excessive pressure in the main-cuff 40 might drive blood out of the muscle, depriving it of the necessary oxygen to function, though such a complication has yet to be reported.

Pyriform fossae—gutters lying on either side of the entrance to the larynx 37, bounded medially by the ary-epiglottic folds and laterally by the membranes stretching between the thyroid horns and the hyoid bones.

Quadrate membrane—the side-walls of the laryngeal vestibule. The quadrate membrane is bounded below by the rima glottidis, posteriorly by the ary-epiglottic folds, and anteriorly by the epiglottis 35.

Rima glottidis—the space between the vocal cords.

Soft palate 195—a muscular wedge of tissue extending posteriorly from the posterior edge of the hard palate 192. The surfaces of the soft palate 195 converge to the mid-line posteriorly and distally to end in a mid-line triangular structure known as the uvula. The soft palate 195 acts like a bridge arching across the space separating the nasal cavity from the rest of the pharynx 197 and completely closes this gap during swallowing. Insertion of the LMA-device 20 relies on the resistance offered by the oral surface of the soft palate 195 to distally guide the distal tip of LMA-device 20.

If the deflated LMA-device 20 is too rigid, or incorrectly deflated, the soft palate 195 cannot guide it downwards, thereby impeding insertion of the LMA-device 20 into the pharynx 197.

Thyroid cartilage—a shield-like structure whose lower border bilaterally overlaps the cricoid cartilage 210. The thyroid cartilage has two posterior-directed horns, the lower of which articulates with the sides of the cricoid 210, so that the whole structure can hinge on the cricoid in the manner of a visor of a helmet. This articulation produced by the crico-thyroid muscle serves to lengthen the vocal cords. The epiglottis 35 is attached to the anterior prominence of the thyroid, also known as the "Adam's Apple", because it projects more sharply in males.

Trachea 36—the wind-pipe, connected directly to the lower rim of the cricoid cartilage 210.

Upper esophageal sphincter 207—guards the entrance to the oesophagus 57. The upper esophageal sphincter 207 is normally closed, even when the LMA-device 20 is in place and pressed into the upper surface of the upper esophageal sphincter. The upper esophageal sphincter 207 can open to approximately 1.5.times.1.0 centimeters.

Vocal cords—folds of tissue which represent the upper free borders of a membrane arising from the cricoid 210, i.e., the crico-vocal membrane. The vocal cords vibrate, lengthen and shorten (for speech), adduct (to prevent soiling of the airway or trachea 36 and to allow coughing), and abduct (to admit air to the lungs). The crico-thyroid muscle lengthens the vocal cords by activating the visor-like hinging action of the crico-thyroid joint. The thyro-arytenoid muscle shortens the vocal cords by pulling the arytenoids 205 anteriorly. The vocalis muscle thickens the vocal cords to affect vibration frequency. The posterior crico-arytenoids abduct the vocal cords. The transverse arytenoids and lateral crico-arytenoids draw the arytenoids 205 together to close the vocal cords.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A laryngeal mask airway device comprising: A. an inflatable cuff, the cuff defining an anterior side, a posterior side, and a central aperture, the cuff being insertable through a mouth of a patient to an inserted location within the patient when the cuff is deflated, the anterior side of the cuff forming a seal around a laryngeal inlet of the patient when the cuff is inflated and when the cuff is at the inserted location; B. a backplate attached to the cuff, the backplate being attached to the cuff only at locations that are closer to the posterior side of the cuff than to the anterior side of the cuff; and C. an airway tube extending from the backplate to a proximal end, the proximal end of the airway tube being disposed outside the patient's mouth when the cuff is at the inserted location, a continuous airway extending from the proximal end of the airway tube to the central aperture of the cuff.

2. A device according to claim 1, the backplate being attached only at locations on the posterior side of the cuff.

3. A device according to claim 1, further including a drainage tube extending from a location near a distal end of the cuff to a location outside the patient's mouth when the cuff is at the inserted location.

4. A device according to claim 3, further including bite plate, the bite plate being connected to the airway and drainage tubes, the bite plate being disposed between the patient's teeth when the cuff is at the inserted location.

5. A device according to claim 1, the cuff further defining a posterior bulge at least when the cuff is inflated.

6. A device according to claim 5, the backplate defining a recess, the posterior bulge extending into the recess at least when the cuff is inflated.

7. A device according to claim 1, the backplate defining a generally tubular opening.

8. A device according to claim 7, the airway tube extending into the tubular opening.

9. A device according to claim 8, the backplate having a strap, a slot being defined between the strap and the tubular opening.

10. A laryngeal mask airway device comprising:
    A. an inflatable cuff, the cuff being insertable through a mouth of a patient to an inserted location within the patient when the cuff is deflated, the cuff forming a seal around a laryngeal inlet of the patient when the cuff is inflated and when the cuff is at the inserted location, the cuff defining a distal end and a central aperture;
    B. a drainage tube extending from a location near the cuff's distal end to a location outside the patient's mouth when the cuff is at the inserted location;
    C. an airway tube having a proximal end, a continuous airway extending from the proximal end of the airway tube to the central aperture of the cuff, the proximal end of the airway tube being disposed outside the patient's mouth when the cuff is at the inserted location; and
    D. a bite-plate connected to the airway and drainage tubes, the bite plate being disposed between the patient's teeth when the mask portion is at the inserted location.

11. A device according to claim 10, including a backplate attached to the cuff.

12. A device according to claim 11, the cuff defining an anterior side and a posterior side, the backplate being attached to the cuff at locations closer to the posterior side of the cuff than to the anterior side of the cuff.

13. A device according to claim 11, the backplate defining a generally tubular opening 14. A device according to claim 13, the airway tube extending into the tubular opening.

15. A device according to claim 14, the backplate having a strap, a slot being defined between the strap and the tubular opening.

16. A device according to claim 10, the cuff further defining a posterior bulge at least when the cuff is inflated.

17. A device according to claim 16, the backplate defining a recess, the posterior bulge extending into the recess at least when the cuff is inflated.

18. A laryngeal-mask airway device comprising:
    A. an inflatable cuff, the cuff defining an anterior side, a posterior side, a proximal end, a distal end, and a central aperture, the proximal end of the cuff defining a posterior bulge at least when the cuff is inflated, the posterior bulge extending in a direction away from the anterior side, the cuff being insertable through a mouth of a patient to an inserted location within the patient when the cuff is deflated, the anterior side of the cuff forming a seal around a laryngeal inlet of the patient when the cuff is inflated and when the cuff is at the inserted location;
    B. a backplate attached to the cuff, the backplate defining a recess, the protrusion extending into the recess at least when the cuff is inflated; and C. an airway tube extending from the backplate to a proximal end, the proximal end of the airway tube being disposed outside the patient's mouth when the cuff is at the inserted location, a continuous airway extending from the proximal end of the airway tube to the central aperture of the cuff.

19. A device according to claim 18, the backplate being attached to the cuff at locations closer to the posterior side of the cuff than to the anterior side of the cuff.

20. A device according to claim 19, the backplate being attached to the posterior side of the cuff.

21. A device according to claim 18, further including a drainage tube extending from a location near the cuff's distal end to a location outside the patient's mouth when the cuff is at the inserted location.

22. A device according to claim 21, further including bite plate, the bite plate being connected to the airway and drainage tubes, the bite plate being disposed between the patient's teeth when the cuff is at the inserted location.

23. A device according to claim 18, the backplate defining a generally tubular opening.

24. A device according to claim 23, the airway tube extending into the tubular opening.

25. A device according to claim 24, the backplate having a strap, a slot being defined between the strap and the tubular opening.

26. A laryngeal-mask airway device comprising:
A. an inflatable cuff, the cuff being insertable through a mouth of a patient to an inserted location within the patient when the cuff is deflated, the cuff forming a seal around a laryngeal inlet of the patient when the cuff is inflated and when the cuff is at the inserted location, the cuff defining a central aperture;
B. a backplate attached to the cuff, the backplate defining a generally tubular opening, the backplate having a strap, a slot being defined between the strap and the tubular opening; and
C. an airway tube extending from the tubular opening of the backplate to a proximal end, the proximal end of the airway tube being disposed outside the patient's mouth when the cuff is at the inserted location, a continuous airway extending from the proximal end of the airway tube to the central aperture of the cuff.

27. A device according to claim 26, further including a drainage tube extending from a location near a distal end of the cuff to a location outside the patient's mouth when the cuff is at the inserted location.

28. A device according to claim 27, the drainage tube extending through the tubular opening.

29. A device according to claim 27, further including bite plate, the bite plate being connected to the airway and drainage tubes, the bite plate being disposed between the patient's teeth when the cuff is at the inserted location.

30. A device according to claim 26, the cuff defining an anterior side and a posterior side, the backplate being attached to the cuff at locations closer to the posterior side of the cuff than to the anterior side of the cuff.

31. A device according to claim 30, the backplate being attached to the posterior side of the cuff.

32. A device according to claim 26, the cuff further defining a posterior bulge at least when the cuff is inflated.

33. A device according to claim 32, the backplate defining a recess, the posterior bulge extending into the recess at least when the cuff is inflated.

\* \* \* \* \*